(12) United States Patent
Suddaby

(10) Patent No.: US 11,331,196 B2
(45) Date of Patent: May 17, 2022

(54) EXPANDABLE INTERVERTEBRAL IMPLANT FOR TREATMENT OF SCOLIOSIS

(71) Applicant: Loubert S. Suddaby, Orchard Park, NY (US)

(72) Inventor: Loubert S. Suddaby, Orchard Park, NY (US)

( * ) Notice: Subject to any disclaimer, the term of this patent is extended or adjusted under 35 U.S.C. 154(b) by 165 days.

(21) Appl. No.: 16/272,030

(22) Filed: Feb. 11, 2019

(65) Prior Publication Data

US 2019/0167441 A1 Jun. 6, 2019

Related U.S. Application Data

(63) Continuation-in-part of application No. 15/787,163, filed on Oct. 18, 2017, now Pat. No. 10,792,165.

(51) Int. Cl.
*A61F 2/44* (2006.01)
*A61F 2/30* (2006.01)

(52) U.S. Cl.
CPC .......... *A61F 2/4425* (2013.01); *A61F 2/447* (2013.01); *A61F 2/4455* (2013.01); *A61F 2002/30019* (2013.01); *A61F 2002/30329* (2013.01); *A61F 2002/30537* (2013.01); *A61F 2002/30556* (2013.01); *A61F 2002/30579* (2013.01); *A61F 2002/30593* (2013.01); *A61F 2002/443* (2013.01)

(58) Field of Classification Search
None
See application file for complete search history.

(56) References Cited

U.S. PATENT DOCUMENTS

| | | | |
|---|---|---|---|
| 5,483,463 A | 1/1996 | Qin et al. | |
| 5,554,191 A | 9/1996 | Lahille et al. | |
| 5,683,463 A | 11/1997 | Godefroy et al. | |
| 6,159,244 A | 12/2000 | Suddaby | |
| 6,193,757 B1 * | 2/2001 | Foley ............ | A61F 2/4455 623/17.16 |
| 6,395,031 B1 | 5/2002 | Foley et al. | |
| 6,500,205 B1 | 12/2002 | Michelson | |
| 6,652,584 B2 | 11/2003 | Michelson | |
| 6,709,458 B2 | 3/2004 | Michelson | |
| 6,793,679 B2 | 9/2004 | Michelson | |

(Continued)

OTHER PUBLICATIONS

SpineSource launches an expandable lumbar interbody cage in the US, https://goo.gl/images/52SER5; Subject: I found this on Google Images from www.alibaba.com; Expandable Lumbar Peek Cage—Buy Spinal Cage,Peek Cage, Cage Product on Alibaba.com https://goo.gl/images/Lw8YDc, last accessed Jan. 14, 2019.

*Primary Examiner* — Tessa M Matthews
(74) *Attorney, Agent, or Firm* — Simpson & Simpson, PLLC; Michael Nicholas Vranjes

(57) ABSTRACT

An expandable intervertebral implant, including a support component, an inferior component, including a first proximate end connected to the support component, a first distal end, a first top surface, and a first bottom surface, a superior component, including a second proximate end connected to the support component, a second distal end, a second top surface, and a second bottom surface, and a balloon connected to the first top surface and the second bottom surface and operatively arranged to expand the expandable intervertebral implant.

20 Claims, 18 Drawing Sheets

(56) References Cited

U.S. PATENT DOCUMENTS

| | | |
|---|---|---|
| 6,808,537 B2 | 10/2004 | Michelson |
| 6,814,756 B1 | 11/2004 | Michelson |
| 6,833,006 B2 | 12/2004 | Foley et al. |
| 6,962,606 B2 | 11/2005 | Michelson |
| 6,972,035 B2 | 12/2005 | Michelson |
| 7,008,453 B1 | 3/2006 | Michelson |
| 7,118,579 B2 | 10/2006 | Michelson |
| 7,118,598 B2 | 10/2006 | Michelson |
| 7,270,682 B2 | 9/2007 | Frigg et al. |
| 7,608,107 B2 | 10/2009 | Michelson |
| 7,655,027 B2 | 2/2010 | Michelson |
| 7,655,042 B2 | 2/2010 | Foley et al. |
| 7,655,046 B2 | 2/2010 | Dryer et al. |
| 7,892,286 B2 | 2/2011 | Michelson |
| 7,922,729 B2 | 4/2011 | Michelson |
| 7,972,382 B2 * | 7/2011 | Foley .............. A61F 2/4455 623/17.12 |
| 7,993,403 B2 | 8/2011 | Foley et al. |
| 8,007,534 B2 | 8/2011 | Michelson |
| 8,038,713 B2 | 10/2011 | Ferree |
| 8,075,621 B2 | 12/2011 | Michelson |
| 8,097,034 B2 | 1/2012 | Michelson |
| 8,403,990 B2 | 3/2013 | Dryer et al. |
| 8,470,041 B2 | 6/2013 | Ferree |
| 8,496,706 B2 | 7/2013 | Ragab et al. |
| 8,628,578 B2 | 1/2014 | Miller et al. |
| 8,685,095 B2 | 4/2014 | Miller et al. |
| 8,771,358 B2 | 7/2014 | Michelson |
| 8,778,025 B2 | 7/2014 | Ragab et al. |
| 8,801,789 B2 | 8/2014 | Ferree |
| 8,920,507 B2 | 12/2014 | Malandain |
| 9,716,247 B2 | 7/2017 | Schicktanz et al. |
| 2002/0128713 A1 * | 9/2002 | Ferree .............. A61F 2/4611 623/17.11 |
| 2008/0288073 A1 * | 11/2008 | Renganath .......... A61F 2/4611 623/17.12 |
| 2011/0137420 A1 | 6/2011 | Michelson |
| 2012/0271419 A1 * | 10/2012 | Marik .............. A61F 2/4425 623/17.12 |
| 2016/0354212 A1 * | 12/2016 | Baynham ........... A61F 2/4455 |

\* cited by examiner

EXPANDABLE INTERVERTEBRAL IMPLANT FOR TREATMENT OF SCOLIOSIS

CROSS-REFERENCE TO RELATED APPLICATIONS

This application is filed under 35 U.S.C. § 120 as a continuation-in-part of U.S. patent application Ser. No. 15/787,163, filed on Oct. 18, 2017, which application is hereby incorporated by reference in its entirety.

FIELD

The present disclosure relates to orthopedic surgery, and more particularly to an expandable intervertebral implant serving to improve alignment between vertebral elements of the spine affected by an abnormal curvature due to disc degeneration or scoliosis.

BACKGROUND

The spinal column, or backbone, is one of the most important parts of the body. It provides the main support, allowing us to stand upright, bend, and twist. As shown in FIG. 1, thirty three (33) individual bones interlock with each other to form the spinal column. The vertebrae are numbered and divided into regions. The cervical vertebrae C1-C7 form the neck, support the head and neck, and allow nodding and shaking of the head. The thoracic vertebrae T1-T12 join with the ribs to form the rib cage. The five lumbar vertebrae L1-L5 carry most of the weight of the upper body and provide a stable center of gravity when a person moves. Five vertebrae of the sacrum S and four of the coccyx C are fused. This comprises the back wall of the pelvis. Intervertebral discs are located between each of the mobile vertebra. Intervertebral discs comprise a thick outer layer with a crisscrossing fibrous structure annulus A that surrounds a soft gel-like center, the nucleus N. Discs function like shock-absorbing springs. The annulus pulls the vertebral bodies together against the elastic resistance of the gel-filled nucleus. When we bend, the nucleus acts like a ball bearing, allowing the vertebral bodies to roll over the incompressible gel. Each disc works in concert with two facet joints, forming a spinal motion segment. The biomechanical function of each pair of facet joints is to guide and limit the movement of the spinal motion segment. The surfaces of the joint are coated with cartilage that helps each joint move smoothly. Directly behind the discs, the ring-like vertebral bodies create a vertical tunnel called the spinal canal or neuro canal. The spinal cord and spinal nerves pass through the spinal canal, which protects them from injury. The spinal cord is the major column of nerve tissue that is connected to the brain and serves as an information super-highway between the brain and the body. The nerves in the spinal cord branch off to form pairs of nerve roots that travel through the small openings between the vertebrae and the intervertebral foramens.

Various medical conditions require a surgeon to repair, remove and/or replace the aforementioned discs. For example, in one surgical procedure, known as a discectomy (or diskectomy) with interbody fusion, the surgeon removes the nucleus of the disc and replaces it with an implant. As shown in FIG. 2, it may be necessary, for example, for the surgeon to remove the nucleus of the disc between the L3 and L4 vertebrae. Disc $D_{L3-L4}$ is shown in an enlarged view in FIG. 3. This figure also shows various anatomical structures of the spine, including facets F3A and F4A, facet joint FJ, spinous processes SP3 (not shown) and SP4, transverse processes TP3A and TP4A, and intervertebral foramen IF. FIG. 4 is a top view of the section of the spinal column shown in FIG. 3, with the L3 vertebra removed to expose annulus A and nucleus N of disc $D_{L3-L4}$. Neural canal NC is also shown. FIG. 5 is an anterior perspective view of the section of the spinal column shown in FIG. 4. FIG. 6 is a partial cross-sectional view of the section of the spinal column shown in FIG. 5, taken generally along line 6-6, but with vertebra L3 in place atop disc $D_{L3-L4}$.

One common tool used in these spinal surgical procedures is an endoscope. A representative endoscope 30 is shown in FIG. 7A. Endoscopes are complex biomedical devices. The complexity results from the need for fiberoptic bundles and multiple long narrow channels to be contained within a tubular structure that is constrained by the limited dimensions of the body cavity opening. As shown in FIG. 7A, endoscope 30 broadly comprises light guide connector 31, light guide tube 32, control body 33, and insertion tube 34. As will be described infra, the inflatable abrading device of the embodiment is introduced into the disc space via insertion tube 34. As shown in FIG. 7B, surgeon 40 uses the endoscope both to observe and guide the procedure via monitor 41, and to introduce and manipulate surgical instruments and tools during surgery on patient 45.

The endoscope is only one element of the system. Other required elements are a light source, video processor, monitor and water bottle. For the purpose of describing an endoscope in this disclosure, we refer to videoscopes, which represent a newer technology in endoscope development as compared to fiberoptic endoscopes. In videoscopes, the "viewing" fibre bundle is replaced by a miniature charged coupled device (CCD) video camera chip that transmits signals via wires.

Videoscopes include three major sections: connector 31 (sometimes referred to as the "umbilical" section), control body 33 and insertion tube 34. Endoscopes require a watertight internal compartment integrated through all components for electrical wiring and controls, which protects them from exposure to patient secretions during use and facilitates the endoscope being submerged for cleaning and subsequent disinfection. Example embodiments are not intended to be limited to any particular type of endoscope.

Control body 33 provides connections for four systems: the electrical system, the light system, the air and water system, and the suction system. A cable with video signal, light control, and remote switching from the video processor is connected in the electrical system. A watertight cap is required for leak testing and reprocessing. The electrical connector is the only opening to the internal components. The connector is inserted into the light source and directs light via the fiberoptic bundle in the light guide to the distal end of the insertion tube. Air pressure is provided from a pump to the air pipe, and the water bottle is also connected here (there is no water channel or water connection for bronchoscopes). In some endoscope models, the separate air and water channels merge just prior to the distal end where they exit through a single channel. In other models, the air and water channels are totally separate and do not merge. The air and water channels are usually of one millimeter internal diameter, which is too small for brushing. A portable or wall suction system is connected to the suction port. The Universal cord encases the electrical wiring and air, water and suction channels from the connector to the control section. Teflon® (PTFE) tubing is commonly used for channels, and advances in technology have led to more pliable and smooth materials for instrument channels with better anti-adhesion properties. The suction channel size can vary from two to four millimeters internal diameter depending on scope make and model. There is a biopsy port on the side of the insertion tube that allows instruments to be passed down the insertion tube to the distal end (referred to as the instrument channel or biopsy/suction channel).

Control body 33 has moveable knobs that allow the physician to control all scope functions. The angulation control knobs drive the angulation wires and control the bending section at the distal end of the insertion tube, thereby providing two-dimensional angulation. Locking mechanisms are provided to hold the bending section in a specific position. The suction cylinder and valve connects the suction channel to the instrument channel in the insertion tube. By pressing the valve button, suction can be provided to the instrument channel. The air/water cylinder and valve are similar to the suction cylinder/valve except that a two-way button valve is used in a dual channel cylinder thereby providing air or water to the lens at the distal end to wash and insufflate for better vision. Both valves are removable for cleaning. The air and water channels also require a cleaning adapter valve that is to be used at the end of each procedure. Insertion of the cleaning adapter initiates air flow through both air and water channels, and once activated, water is pumped through both channels. The instrument channel port (often referred to as the "biopsy port") is located on the lower part of the control section. It enters the instrument channel at a Y-piece union with the suction channel. A valve is required to close the port so that suctioning may be facilitated. Remote switches present on the top of the control section are usually programmable, allowing control of the video processor (i.e., contrast, iris and image capture functions).

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change, and as such has not benefitted from natural selection as much as have backbones held in a horizontal attitude. As a result, the stresses acting upon the human backbone (or "vertebral column"), are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, five in the lower back or lumbar region, and five in the pelvic or sacral region, which are normally fused together to form the back part of the pelvis. This column of bones is critical for providing structural support for the entire body.

Between the vertebral bones exist soft tissue structures, i.e., discs, composed of fibrous tissue and cartilage that are compressible and act as shock absorbers for sudden downward forces on the upright column. The discs allow the bones to move independently of each other, as well. The repetitive forces which act on these intervertebral discs during repetitive activities of bending, lifting, and twisting cause them to break down or degenerate over time.

Presumably, because of humans' upright posture their intervertebral discs have a high propensity to degenerate. Overt trauma or covert trauma, occurring in the course of repetitive activities, disproportionately affects the more highly mobile areas of the spine. Disruption of a disc's internal architecture leads to bulging, herniation, or protrusion of pieces of the disc and eventual disc space collapse. Resulting mechanical and even chemical irritation of surrounding neural elements (spinal cord and nerves) cause pain, attended by varying degrees of disability. In addition, loss of disc space height relaxes tension on the longitudinal spinal ligaments, thereby contributing to varying degrees of spinal instability such as spinal curvature. Asymmetric loss of disc space height with degeneration causes adult degenerative scoliosis.

The time-honored method of addressing the issues of neural irritation and instability resulting from severe disc damage has largely focused on removal of the damaged disc and fusing the adjacent vertebral elements together. Removal of the disc relieves the mechanical and chemical irritation of neural elements, while osseous union (i.e., bone knitting) solves the problem of instability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration or even expulsion or nonunion due to structural failure of the bone or residual degrees of motion that retard or prohibit bony union. Intervertebral prosthesis in various forms has therefore been used to provide immediate stability and to protect and preserve an environment that fosters growth of the grafted bone such that a structurally significant bony fusion can occur.

U.S. Pat. No. 6,159,244 (Suddaby) exhibits an expandable cage capable of nonparallel expansion but require a complex mechanism of ratcheting pillars. The implant disclosed in U.S. Pat. No. 5,483,463 (Qin et al.) is hollow and tubular, with communicating windows in the top and bottom surfaces, which would permit fusion but the design does little to correct scoliosis.

Many interbody devices in present day use, whether expandable or not, are used largely to facilitate interbody fusion in cases of degenerative disc disease and are not specifically designed to correct scoliosis, which is a pathologic curvature of the spine in the coronal or lateral plane that can be of degenerative, congenital, or idiopathic causes.

SUMMARY

According to aspects illustrated herein, there is provided an expandable intervertebral implant, comprising a support component, an inferior component, including a first proximate end connected to the support component, a first distal end, a first top surface, and a first bottom surface, a superior component, including a second proximate end connected to the support component, a second distal end, a second top surface, and a second bottom surface, and a balloon connected to the first top surface and the second bottom surface and operatively arranged to expand the expandable intervertebral implant.

According to aspects illustrated herein, there is provided an expandable intervertebral fusion implant, comprising a support component, at least one inferior component, including a first proximate end connected to the support component, a first distal end, a first top surface, a first bottom surface, and a first aperture, at least one superior component, including a second proximate end connected to the support component, a second distal end, a second top surface, a second bottom surface, and a second aperture, and an expansion mechanism arranged between the first top surface and the second bottom surface and operatively arranged to be expanded to displace the at least one superior component relative to the at least one inferior component.

According to aspects illustrated herein, there is provided an expandable intervertebral implant, comprising a support component, an inferior component, including a first proximate end connected to the support component, a first distal end, a first top surface, and a first bottom surface, a superior component, including a second proximate end connected to the support component, a second distal end, a second top surface, and a second bottom surface, and a wedging component operatively arranged to be slid along the first top surface and the second bottom surface and expand the expandable intervertebral implant.

According to aspects illustrated herein, there is provided an expandable intervertebral implant, comprising a support component, at least one inferior component, including a first proximate end connected to the support component, a first distal end, a first top surface, and a first bottom surface, at least one superior component, including, a second proximate end connected to the support component, a second distal end, a second top surface; and a second bottom surface, and a wedging component operatively arranged to be slid along the first top surface and the second bottom surface and expand the expandable intervertebral implant.

It is the object of this disclosure to provide for an expandable intervertebral implant having two vertebral endplate contact surfaces connected in a pivotal fashion which can be separated from each other when a third component is wedged between them along their longitudinal axis.

This disclosure relates to an expandable intervertebral fusion implant serving to improve alignment between vertebral elements of the spine affected by an abnormal curvature due to disc degeneration or scoliosis, thereby facilitating the development of a bony union between them and thus fostering proper spinal alignment and thus long term spinal stability.

It is an object of this disclosure to provide for an expandable intervertebral fusion implant that is both simple to manufacture and simple to use in daily clinical surgical practice.

It is also an object of this disclosure that this device serve specifically to correct local spinal alignment issues between adjacent vertebral endplates such that scoliosis or abnormal curvature of the spine can be addressed through a minimally invasive approach.

According to aspects illustrated herein, there is provided a pair of endplate support elements, which are generally rectangular, joined together pivotally at one end. The pivotal end of the implant has vertical separation struts that are of variable length with interspace roughly representing the height of the normal disc space at the level to be addressed.

The distal or non-pivotal end of the implant has two rectangular elements juxtaposed in close proximity, i.e., not separated by a vertical member or strut, such that they form a wedge shape akin to that of a dull knife blade or an adze.

The implant further comprises a third element in the form of a wedging member. The wedging member is inserted into the pivotal end of the implant, which can be advanced along the axis of the longitudinal axis of the rectangular members, once they are positioned across a disc space that has undergone discectomy.

The wedging member is preferably substantially cylindrical in shape, with a diameter that approximates the vertical struts at the pivotal end. The cylindrical wedge component is placed between the rectangular elements at the pivotal end once the construct has been placed across a disc space and then is impelled toward the non-pivotal end, such that said distal elements are separated from each other as the wedging element is advanced.

When the wedging cylinder has reached the distal or non-pivotal end of the implant, the rectangular elements become more or less parallel to each other by virtue of the diameter of the cylinder approximating the height of the pivotal end.

Each rectangular element will harbor apertures or perforation such that bony or biologic materials placed within the implant, once expanded by the cylinder, will have close apposition to adjacent vertebral endplates and hence can foster interbody fusion.

Once the wedging cylinder has reached the distal end of the implant, it will be locked into position by a stop which prevents it from simply rolling back to its start point. By securing the wedging cylinder in such a fashion, implant stability is preserved.

It should be noted that, in an example embodiment, the pivotal end of the implant will be anchored to the vertebrae with one or more bone screws to prevent expulsion of the implant as the wedge cylinder is advanced and as the implant changes from a triangular or trapezoidal shape to a more rectangular configuration.

The present disclosure provides not only for an expandable interbody fusion implant, but also for an implant that can be placed via a lateral minimally invasive approach, from the easier access or convex side of a scoliotic spine, and restore the normal parallel attitude of adjacent endplates prior to insertion of final biologic fusion products.

Additionally, because the initial configuration of the implant is wedge shaped, it can be used to breach and release the contralateral annulus and associated ligamentous structures, should this be desired.

By using the implant at each spinal segment containing non-parallel adjacent endplates, spinal alignment can be restored through a minimally invasive or lateral lumbar interbody fusion (XLIF) surgical approach.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

Figure 1:
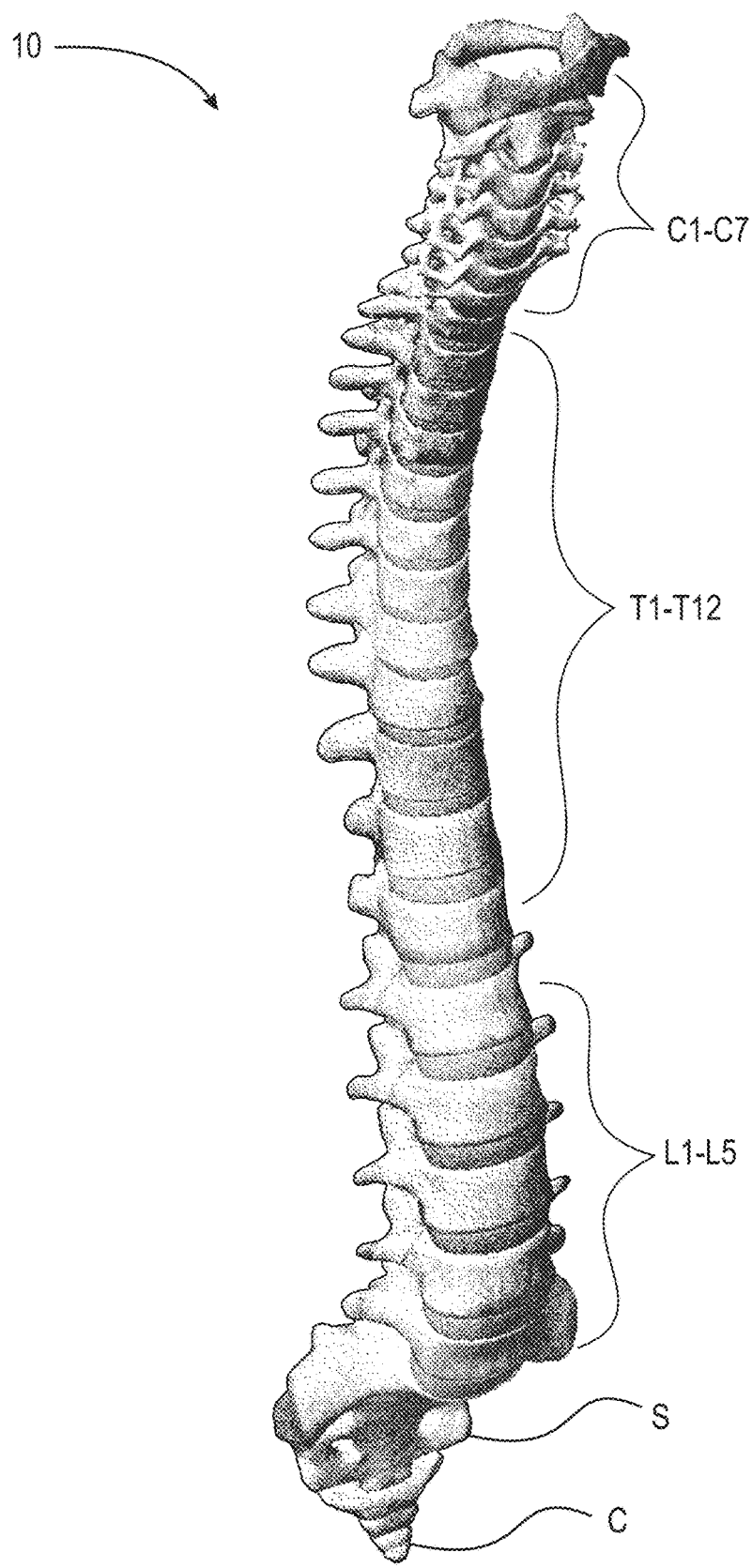
FIG. 1 is an anterior perspective view of a spinal column.
Figure 2:
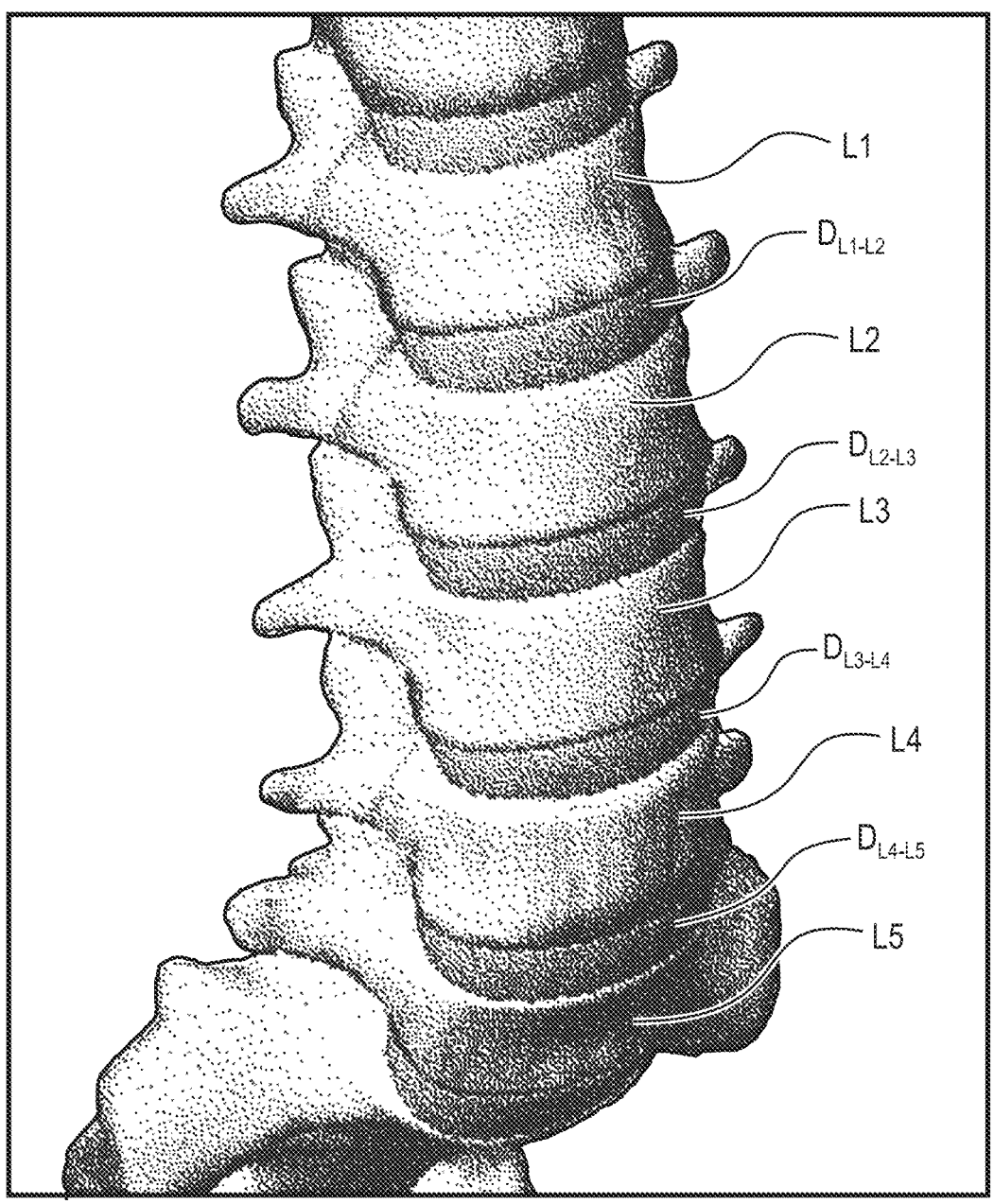
FIG. 2 is an anterior perspective view of the lumbar section of the spinal column shown in FIG. 1.
Figure 3:
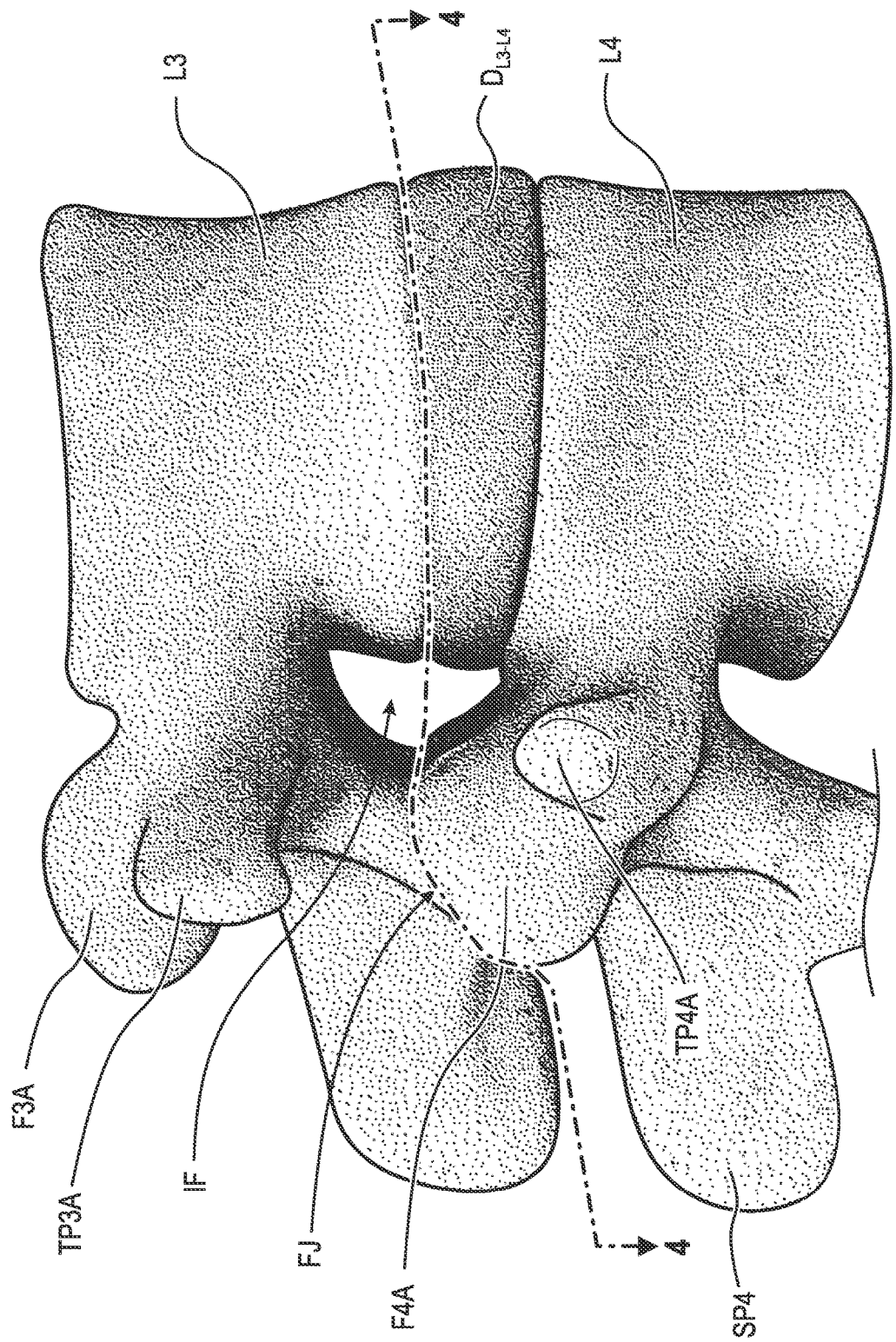
FIG. 3 is a lateral perspective view of two vertebrae, a disc, and related spinal anatomy.
Figure 4:
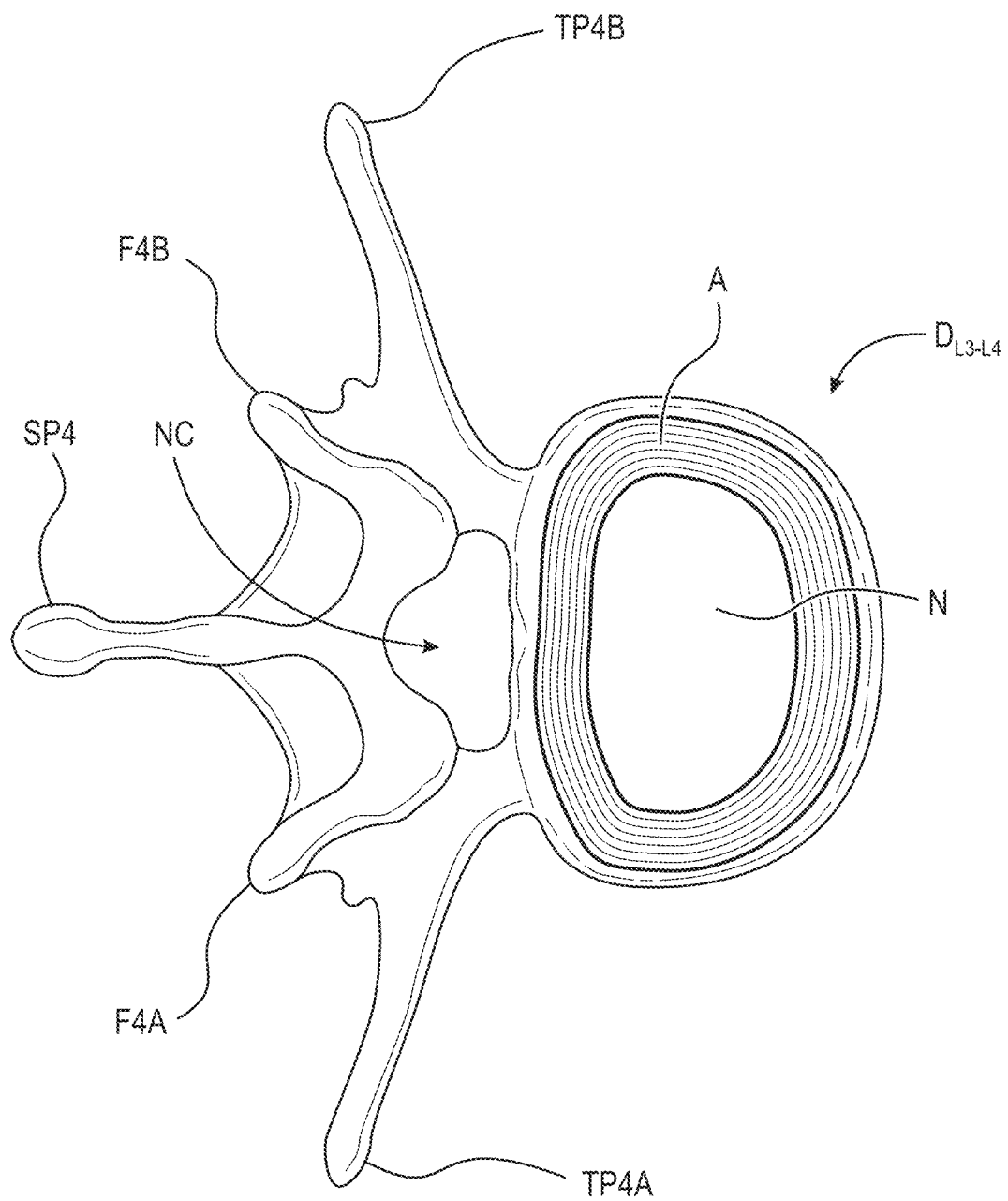
FIG. 4 is a top view of a section of the spinal column, taken generally along line 4-4 in FIG. 3.
Figure 5:
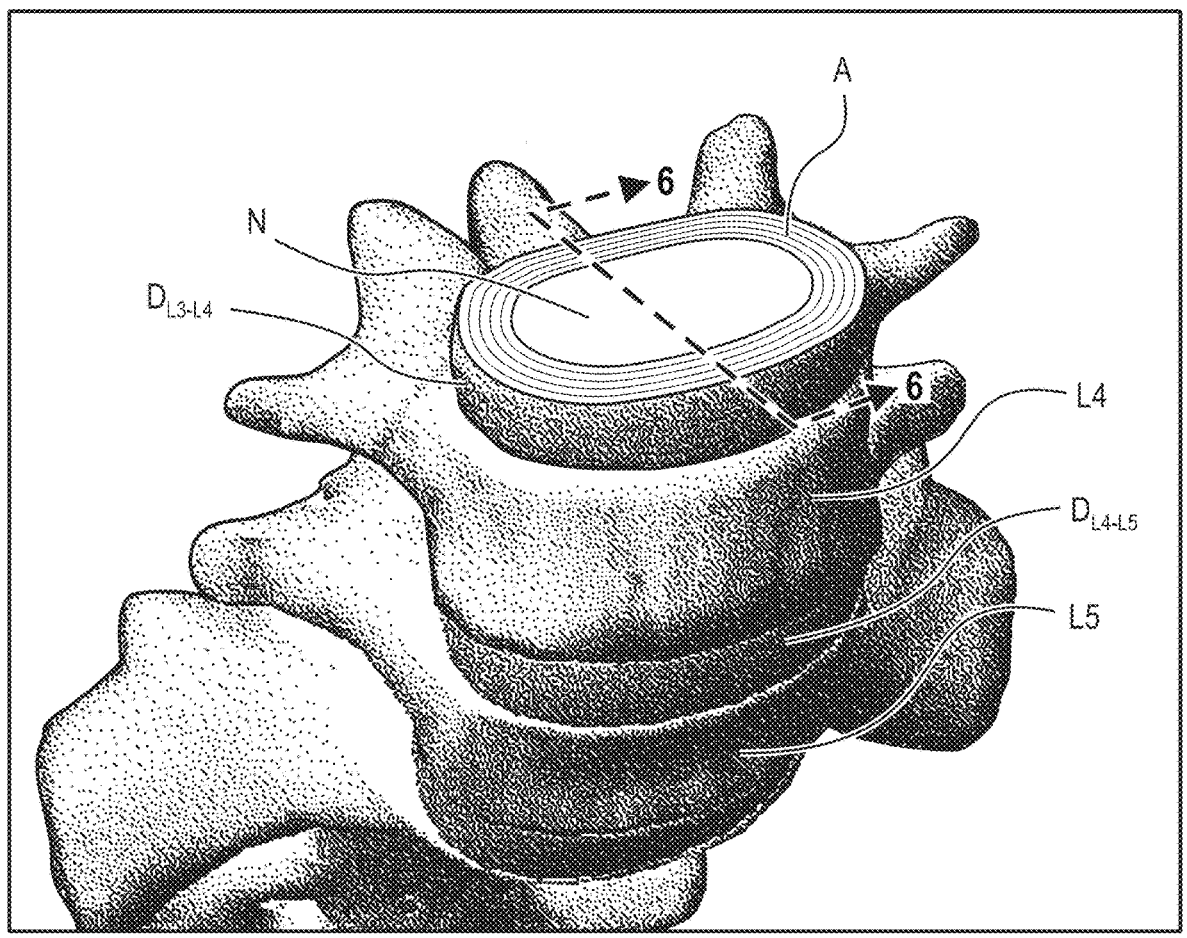
FIG. 5 is an enlarged anterior perspective view of the spinal column shown in FIG. 2, except with the top vertebra and all other structure above the top vertebra removed.
Figure 6:
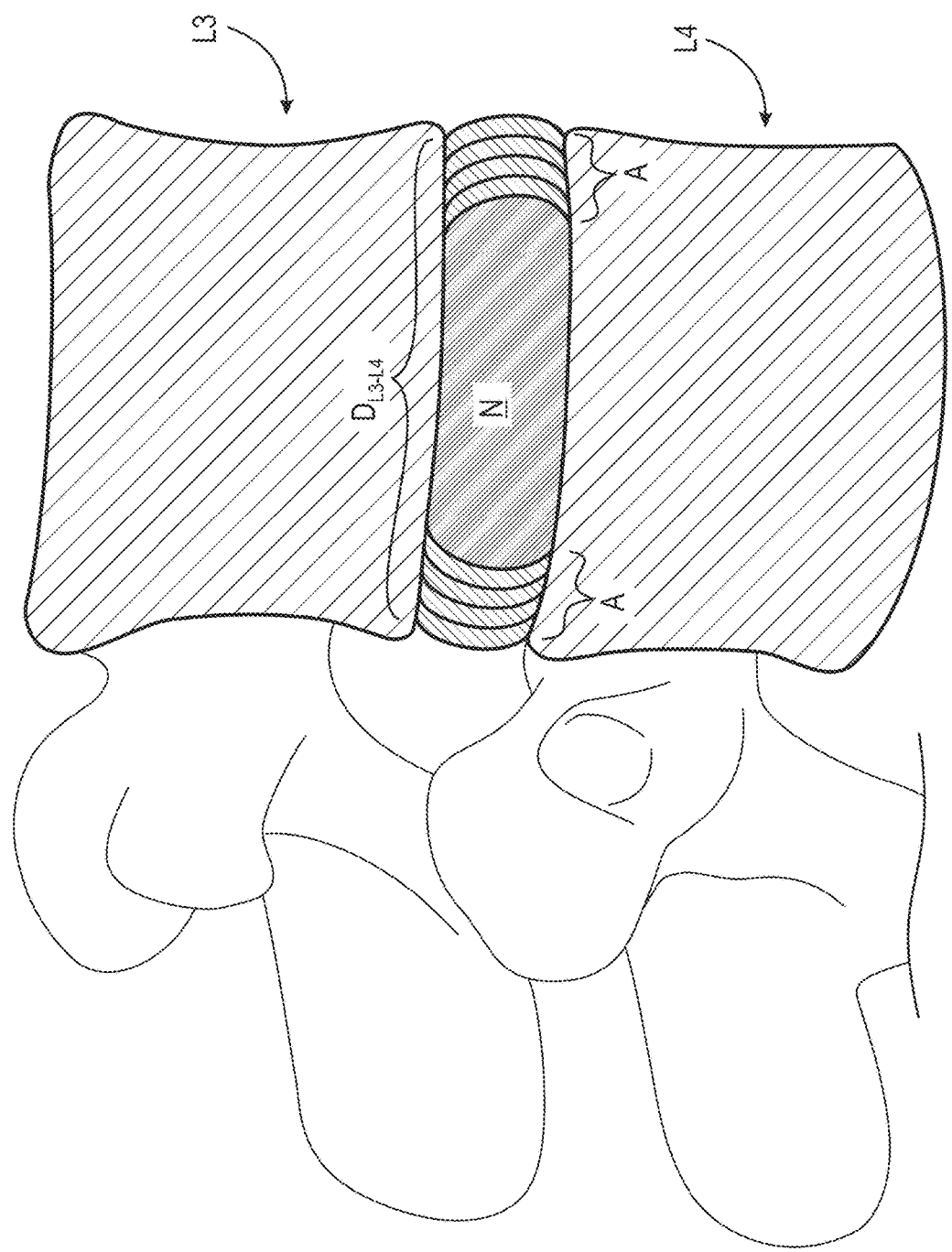
FIG. 6 is a partial cross-sectional view of the top and bottom vertebrae and disc, taken generally along line 6-6 in FIG. 5.
Figure 7:
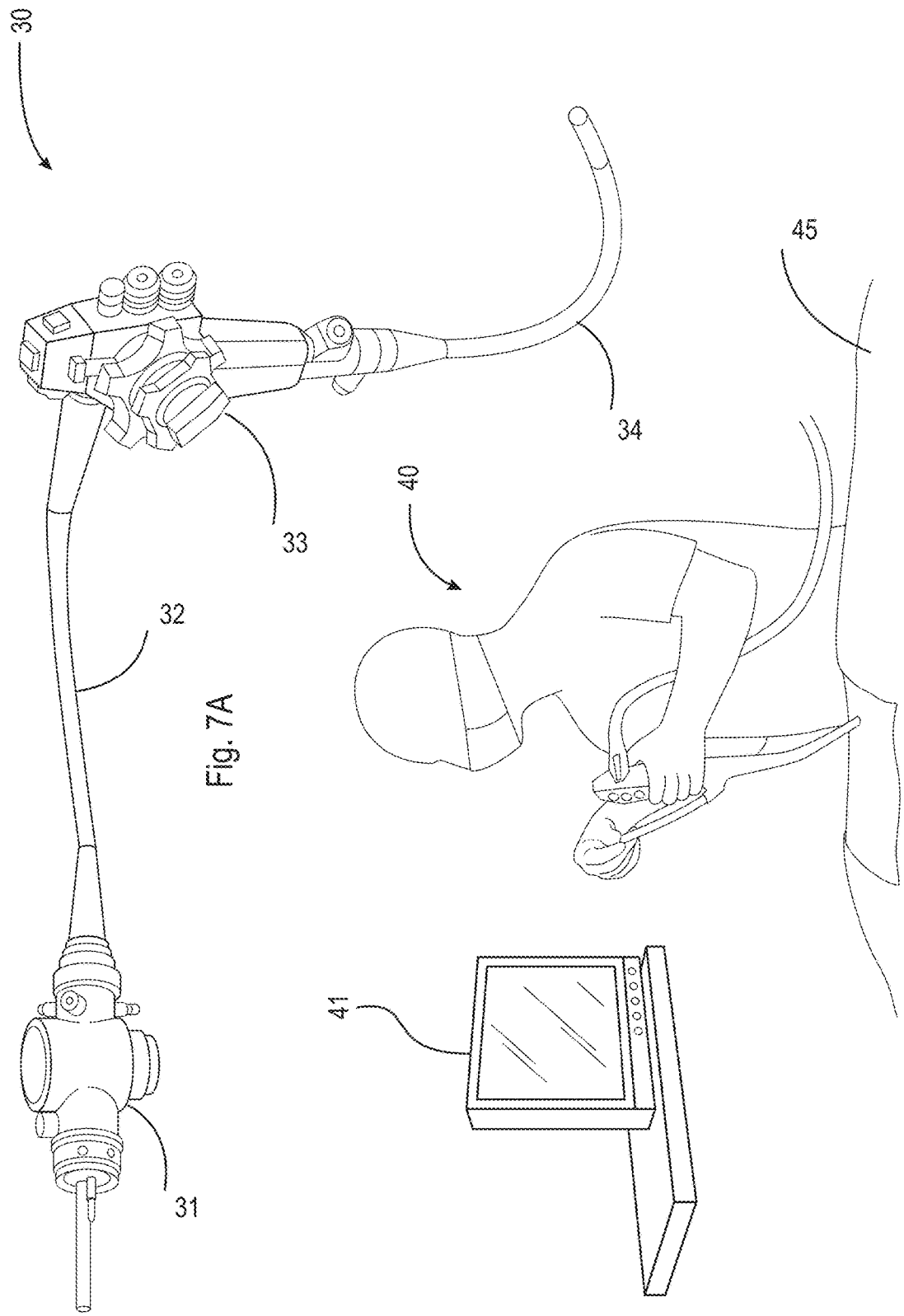
FIG. 7A is a view of a typical endoscope.
FIG. 7B illustrates use of the endoscope shown in FIG. 7A by a surgeon performing a discectomy (diskectomy)

Adverting now to the figures, and as described previously, FIGS. 1-6 depict various parts and sections of spinal anatomy, and FIGS. 7A and 7B depict a typical endoscope for use by a surgeon on a patient.

Figure 8:
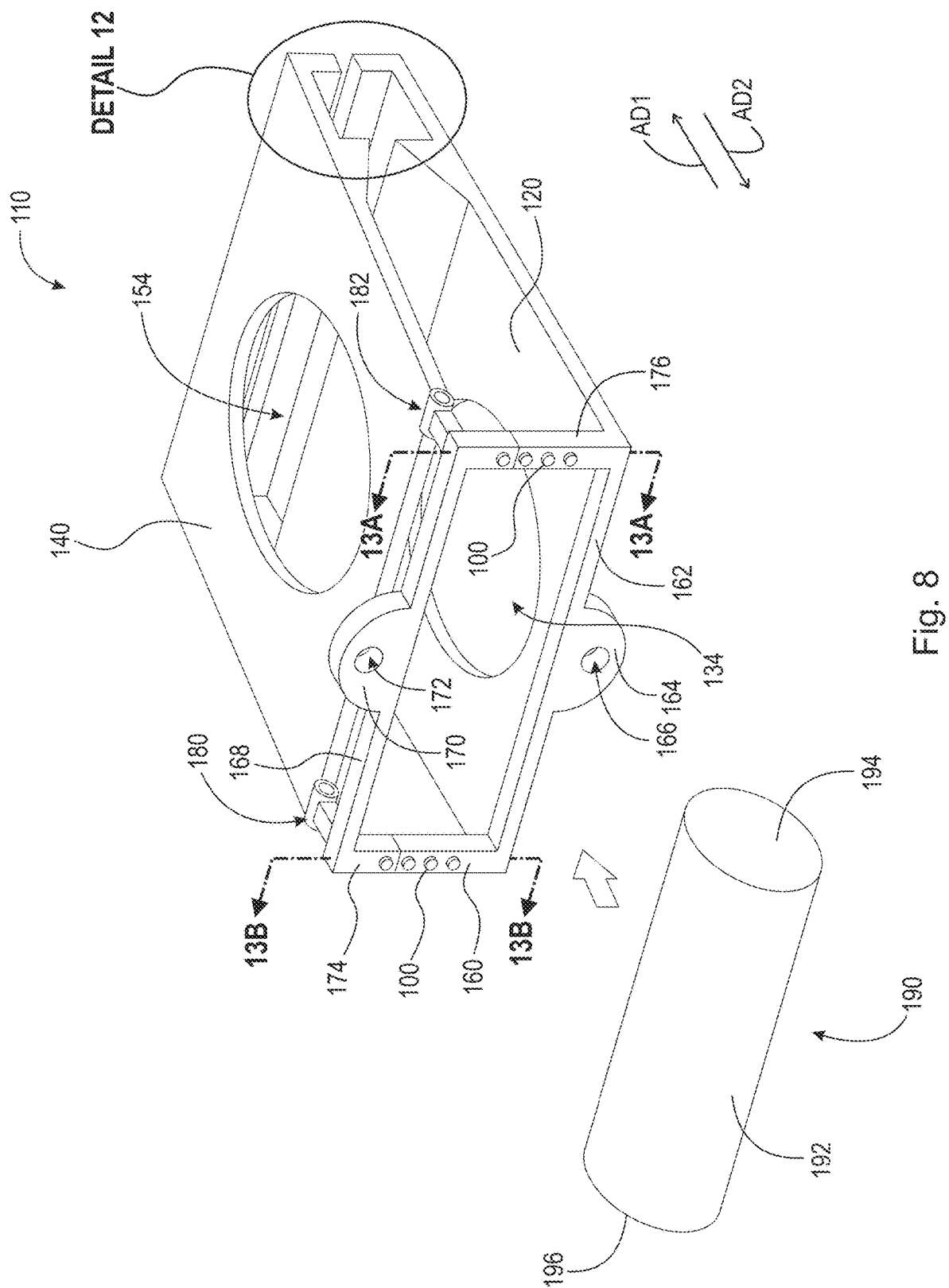
FIG. 8 is a top perspective view of an expandable intervertebral implant, in a collapsed state.
Figure 9A:
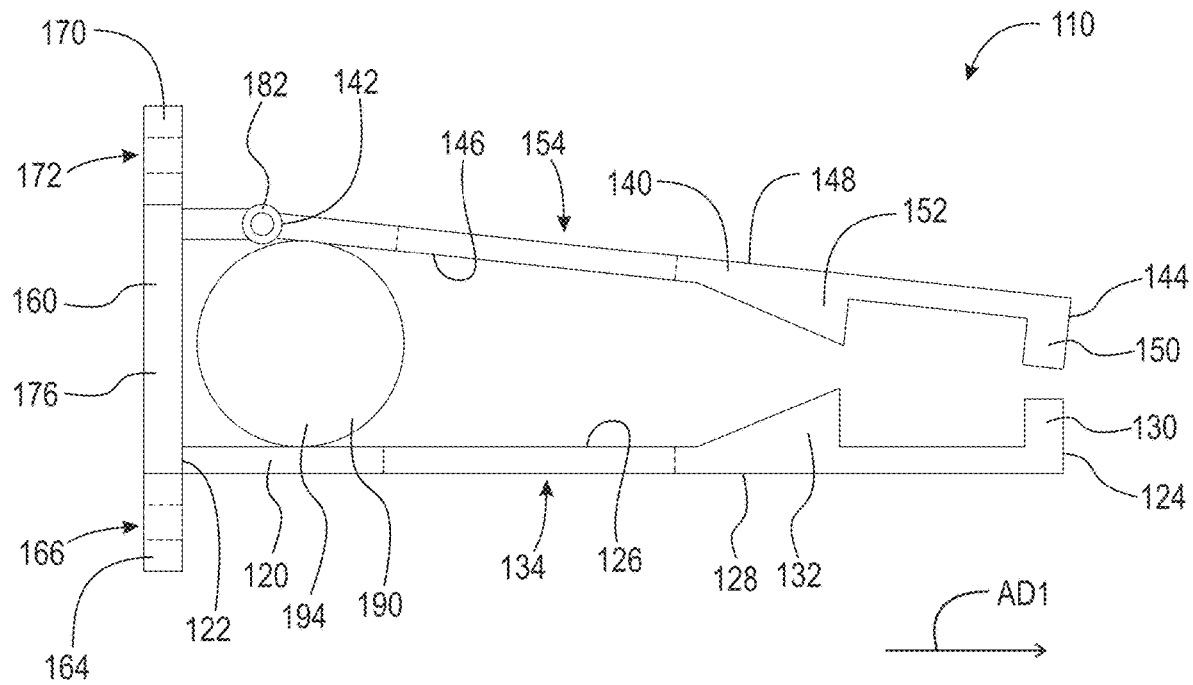
FIG. 9A is a side elevational view of the expandable intervertebral implant shown in FIG. 8.
Figure 9B:
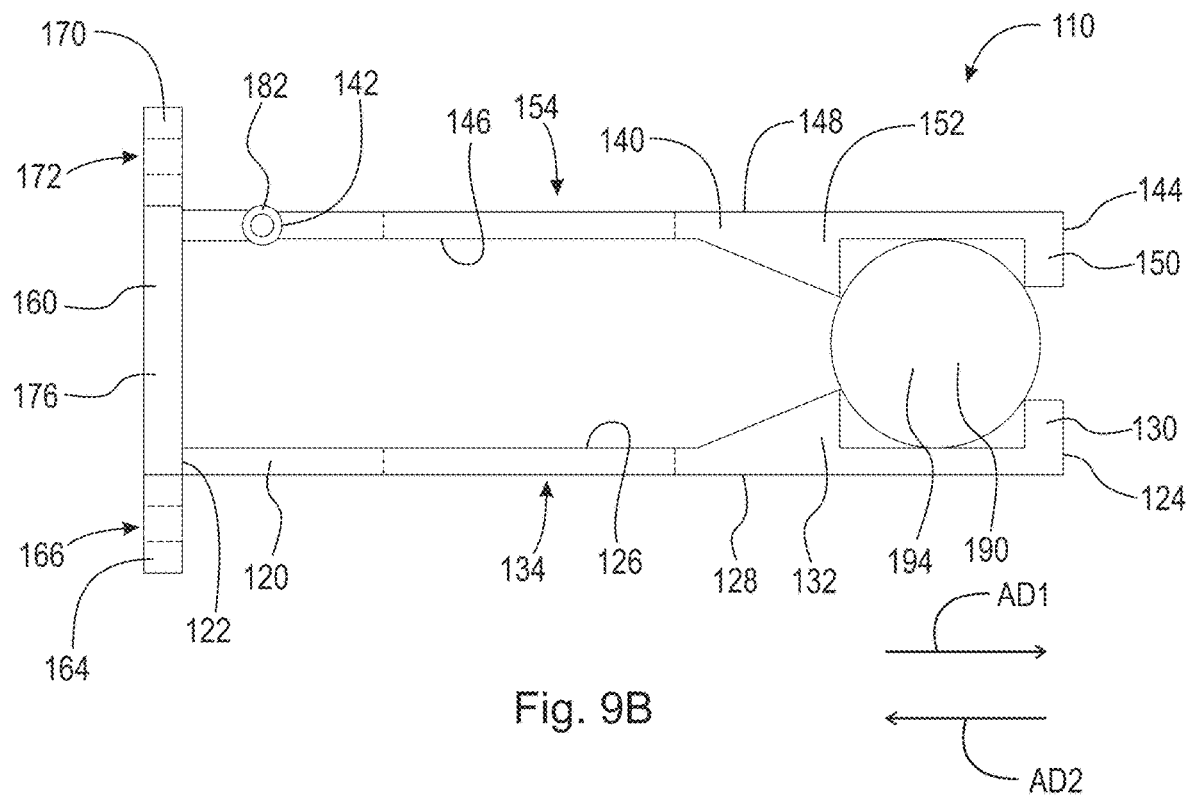
FIG. 9B is a side elevational view of the expandable intervertebral implant shown in FIG. 8 in an expanded state.

FIG. 8 is a top perspective view of expandable intervertebral implant 110, in a collapsed state. FIG. 9A is a side elevational view of expandable intervertebral implant 110 in a collapsed state. FIG. 9B is a side elevational view of expandable intervertebral implant 110 in an expanded state. Expandable intervertebral implant 110 generally comprises inferior component 120, superior component 140, support component 160, and wedging component 190.

Inferior component 120 comprises end 122, end 124, top surface 126, and bottom surface 128. Inferior component 120 is connected to support component 160 at end 122. In an example embodiment, inferior component 120 is secured to cross member 162 such that it is perpendicular to vertical members 174 and 176. In an example embodiment, inferior component 120 is secured to support component 160 at a non-perpendicular angle to vertical members 174 and 176. Inferior component 120 may further comprise aperture 134, which extends from top surface 126 to bottom surface 128. Aperture 134 allows bony or biologic materials placed within expandable intervertebral implant 110, once expanded, to have close apposition to adjacent vertebral endplates and thereby foster interbody fusion. Top surface 126 further comprises lip 130 and stop 132. Lip 130 extends upward from top surface 126 and is arranged generally proximate end 124. Lip 130 is arranged as a boundary for wedging component 190 (i.e., to keep wedging component 190 within expandable intervertebral implant 110). Stop 132 extends upward from top surface 126 and is arranged axially inward (i.e., in axial direction AD2) from end 124 as shown in the figures. Stop 132 is designed to allow wedging component 190 to move in axial direction AD1, but once beyond stop 132, to prevent movement of wedging component 190 in axial direction AD2 and maintain its position as shown in FIG. 9B.

Superior component 140 comprises end 142, end 144, top surface 148, and bottom surface 146. Superior component 140 is connected to support component 160 generally at end 142. Specifically, superior component 140 is connected to hinges 180 and 182, and hinges 180 and 182 are connected to support component 160. In an example embodiment, hinges 180 and 182 are connected to cross-member 168. In an example embodiment, expandable intervertebral implant 110 comprises one or more hinges. Superior component 140 may further comprise aperture 154, which extends from top surface 148 to bottom surface 146. Aperture 154 allows bony or biologic materials placed within expandable intervertebral implant 110, once expanded, to have close apposition to adjacent vertebral endplates and thereby foster interbody fusion. Bottom surface 146 further comprises lip 150 and stop 152. Lip 150 extends downward from bottom surface 146 and is arranged generally proximate end 144. Lip 150 is arranged as a boundary for wedging component 190 (i.e., to keep wedging component 190 within expandable intervertebral implant 110). Stop 152 extends downward from bottom surface 146 and is arranged axially inward (i.e., in axial direction AD2) from end 144 as shown in the figures. Stop 152 is designed to allow wedging component 190 to move in axial direction AD1, but once beyond stop 152, to prevent movement of wedging component 190 in axial direction AD2 and maintain its position as shown in FIG. 9B.

It should be appreciated that the orientation of hinges 180 and 182 can be reversed such that inferior component 120 is hingedly connected to support component 160. In this embodiment, superior component 140 is connected to support component 160. Specifically, end 142 is secured to cross-member 168 such that superior component 140 is generally perpendicular to vertical members 174 and 176. In an example embodiment, superior component 140 can be secured to support component 160 at a non-perpendicular angle (i.e., non-perpendicular to vertical members 174 and 176). Hinges 180 and 182 are secured to cross-member 162 and end 122 of inferior component 120 is secured to hinges 180 and 182. In an example embodiment, both inferior component 120 and superior component 140 are hingedly connected to support component 160.

Support component 160 generally comprises cross-member 162, cross-member 168, vertical member 174, and vertical member 176. Cross-member 162 further comprises flange 164 having through-bore 166 for anchoring expandable intervertebral implant 110 to the vertebrae and prevent expulsion of expandable intervertebral implant 110 as wedging component 190 is advanced therein. Flange 164 extends generally downward from cross-member 162. Cross-member 168 further comprises flange 170 having through-bore 172 for anchoring expandable intervertebral implant 110 to the vertebrae and prevent expulsion of expandable intervertebral implant 110 as wedging component 190 is advanced therein. Flange 168 extends generally upward from cross-member 168. Vertical members 174 and 176 connect cross-member 168 to cross-member 162. Vertical members 174 and 176 are generally adjustable (i.e., can be lengthened or shortened) as will be discussed in greater detail with respect to FIGS. 13A and 13B.

Wedging component 190 is generally cylindrical comprising radially outward facing surface 192, end surface 194, and end surface 196. Wedging component 190 is designed to be inserted into expandable intervertebral implant 110 in axial direction AD1 with end surfaces 194 and 196 generally perpendicular to ends 122 and 124. As wedging component 190 is advanced in expandable intervertebral implant 110, radially outward facing surface 192 slides along top surface 126 and bottom surface 146, thereby forcing superior component 140 upward and away from superior component 120. Once wedging component 190 passes stops 132 and 152, wedging component 190 is prevented from movement in axial direction AD2, unless superior component 140 is forced further in the upward direction, thereby releasing stops 132 and 152 (wedging component 190 can then be removed from expandable intervertebral implant 110). Lips 130 and 150 also provide an axial boundary preventing wedging component 190 from "falling out" of expandable intervertebral implant 110 in axial direction AD1. Inferior component 120 and superior component 140 may further comprise lateral rails for end surfaces 194 and 196 to slide against to help ensure that wedging component 190 does not yaw (i.e., twist or oscillate about a vertical axis) as it is being advanced within expandable intervertebral implant 110 (i.e., keep end surfaces 194 and 196 perpendicular to ends 122 and 124). It should be appreciated that wedging component 190 can be any shape suitable to slide along top surface 126 and bottom surface 146 and expand expandable intervertebral implant 110, such as rectangular prism, elliptical prism, triangular prism, spherical, etc. It should also be appreciated that the size of wedging component 190 should be relative to the vertical height of support component 160. When wedging component 190 is fully inserted in expandable intervertebral implant 110, it is desired that superior component 140 is substantially parallel to inferior component 120. Therefore, the diameter of wedging component 190 should be slightly less than the vertical length of vertical members 174 and 176. Since vertical members 174 and 176 are adjustable, as will be discussed in greater detail below, a variety of sizes of wedging component 190 should be available such that the surgeon can choose the correct size during operation.

Figure 10:
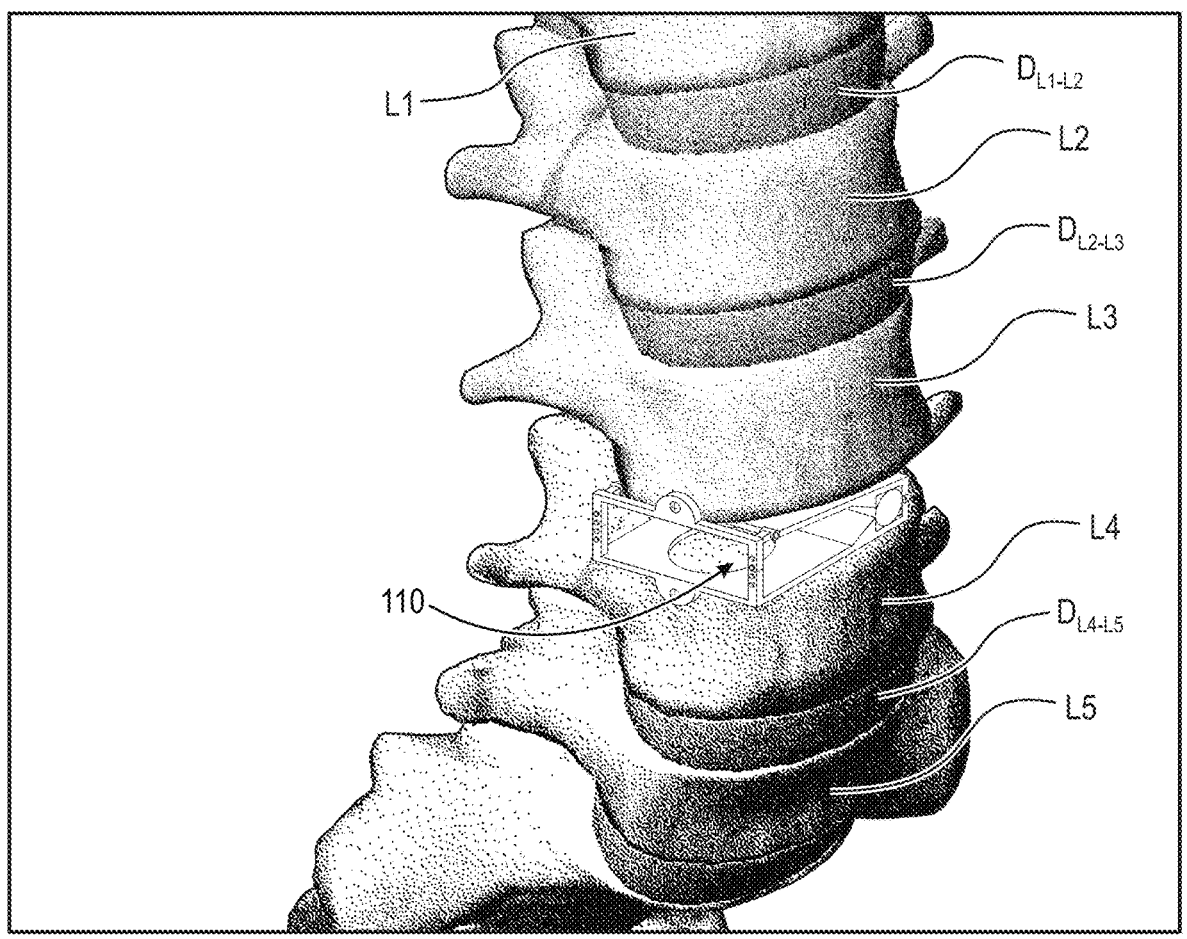
FIG. 10 is an anterior perspective view of a spinal column including the expandable intervertebral implant shown in FIG. 8.
Figure 11B:
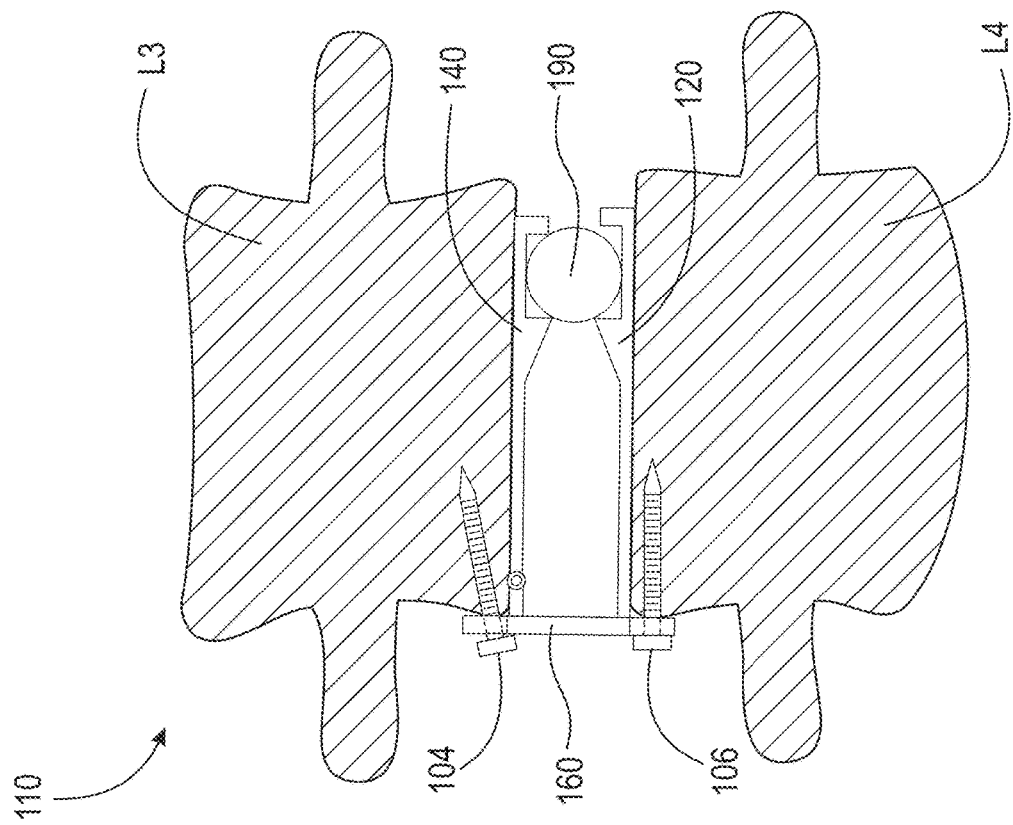
FIG. 11B is a side elevational view of the expandable intervertebral implant shown in FIG. 10 in an expanded state.
Figure 11A:
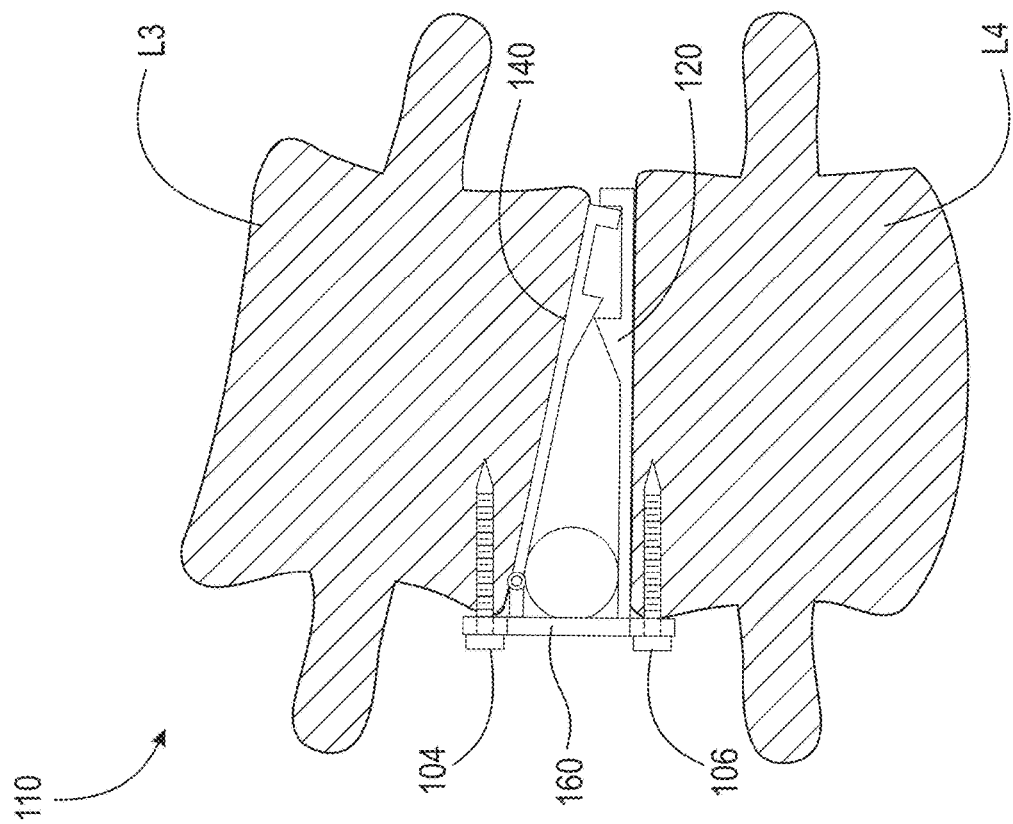
FIG. 11A is a side elevational view of the expandable intervertebral implant shown in FIG. 10 in a collapsed state.

FIG. 10 is an anterior perspective view of a spinal column including expandable intervertebral implant 110. FIG. 11A is a side elevational view of expandable intervertebral implant 110 shown in FIG. 10 in a collapsed state. FIG. 11B is a side elevational view of the expandable intervertebral implant 110 shown in FIG. 10 in an expanded state. Expandable intervertebral implant 110 is inserted into the spinal column between, for example, the L3 and L4 vertebrae, or where disc $D_{L3-L4}$ should be. Expandable intervertebral implant 110 is secured to the vertebrae, for example, by fasteners 104 and 106. In an example embodiment, fastener 104 secures expandable intervertebral implant 110 to lumbar vertebra L3 and fastener 106 secures expandable intervertebral implant 110 to lumbar vertebra L4. Fasteners 104 and 106 may be screws, anchors, bolts, etc., or any other suitable fastening mechanism, including adhesives. Expandable intervertebral implant 110 is then vertically expanded until the desired height is reached. Support component 160 is expanded by lengthening vertical members 174 and 176 to a suitable length, and then a suitable size wedging component 190 is chosen and advanced in expandable intervertebral implant 110 until it is fully expanded. Expandable intervertebral implant 110 is then filled with fusion material and left in situ. It should be appreciated that vertical members 174 and 176 can be adjusted to a suitable length prior to inserting expandable intervertebral implant 110 into the spinal column.

Figure 12A:
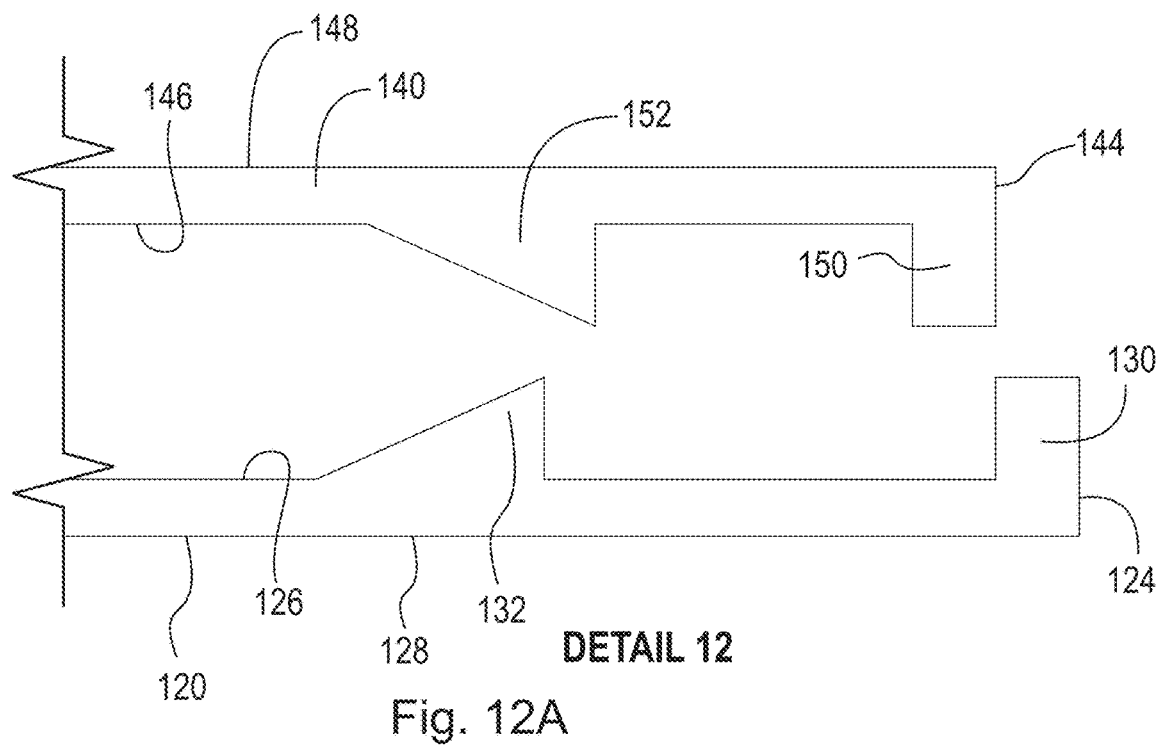
FIG. 12A is a side elevational view of the expandable intervertebral implant taken generally of detail 12 in FIG. 8.
Figure 12B:
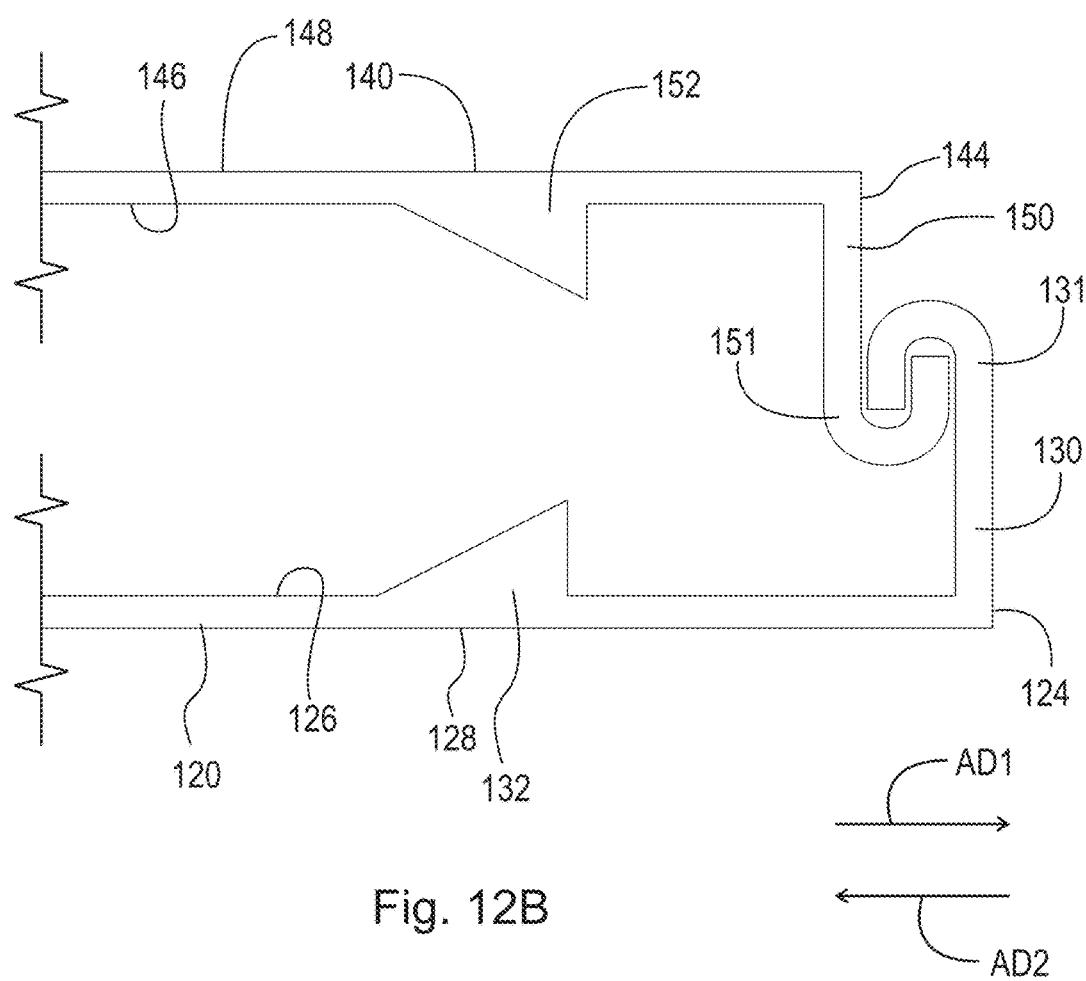
FIG. 12B is a side elevational view of an expandable intervertebral implant.

FIG. 12A is a side elevational view of expandable intervertebral implant 110 taken generally of detail 12 in FIG. 8. FIG. 12B is a side elevational view of an example embodiment of expandable intervertebral implant 110 having hooks attached to the lips. As shown, inferior component 120 further comprises hook 131 connected to the end of lip 130. Similarly, superior component 140 further comprises hook 151 connected to the end of lip 150. Hook 131 is arranged facing axial direction AD1 and hook 151 is arranged facing axial direction AD2, such that superior component 140 can only be separated from inferior component 120 a predetermined distance. Once that predetermined distance is reached, hooks 131 and 151 engage and prevent superior component 140 from separating further from inferior component 120. In an example embodiment, hook 131 is arranged facing axial direction AD2 and hook 151 is arranged facing axial direction AD1. It should be appreciated that any method suitable for preventing excessive vertical displacement of superior component 140 relative to inferior component 120, such as stops, flanges, etc., or a leash component such as a string or cord of a predetermined length may be used.

Figure 13A:
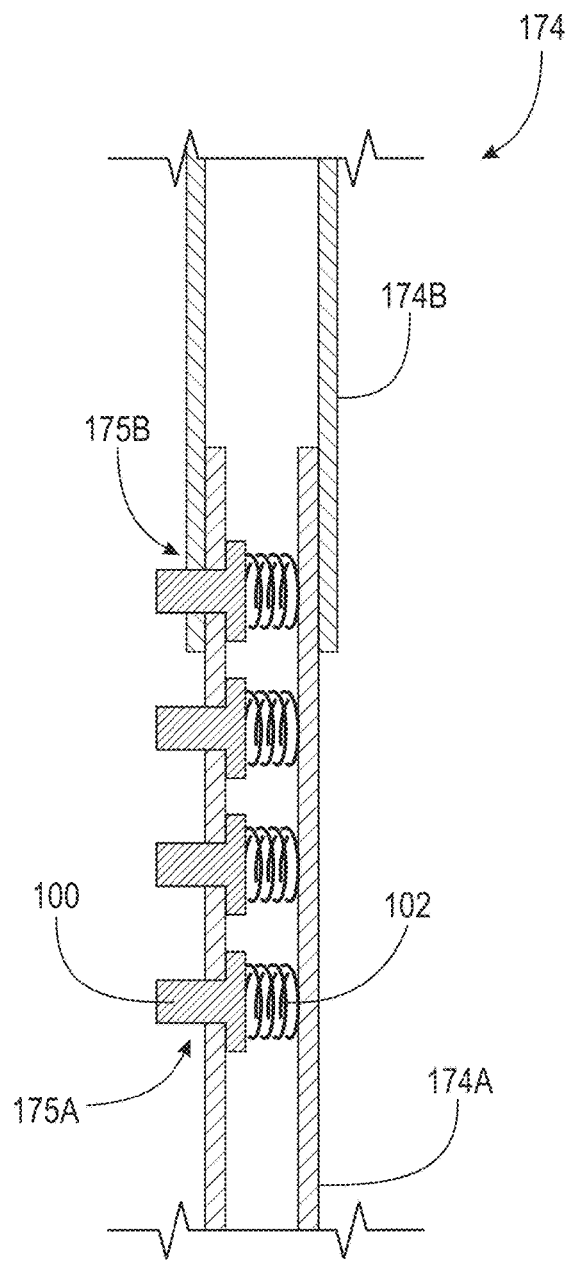
FIG. 13A is a cross-sectional view of a vertical member taken generally along line 13A-13A in FIG. 8.

FIG. 13A is a cross-sectional view of vertical member 174 taken generally along line 13A-13A in FIG. 8. As shown, vertical member 174 comprises inner bar 174A arranged to slidingly engage outer bar 174B (i.e., vertical member 174 is a telescoping bar). In the embodiment shown, inner bar 174A comprises a plurality of pins 100 and corresponding spring members 102. Pins 100 protrude from holes 175A in inner bar 174A, specifically, pins 100 are forced radially outward through holes 175A by spring members 102. Pins 100 are forced radially inward such that inner bar 174A can be slid axially within outer bar 174B. One of pins 100 is aligned with hole 175B in outer bar 174B once the desired length of vertical member 174 is achieved. In an example embodiment, vertical member 174 is cylindrical, inner bar 174A comprises radially outer threading, and outer bar 174B comprises radially inner threading such that the length of vertical member 174 is adjustable by rotating one of inner bar 174A or outer bar 174B relative to the other. It should be appreciated that telescoping members are known in the art and that any suitable telescoping design may be used. This similar locking mechanism (i.e., the push-pins) may be used on cross-members 162 and 168. In an example embodiment, one or more cross-members have a locking mechanism. In an example embodiment, no cross-members have a locking mechanism.

Figure 13B:
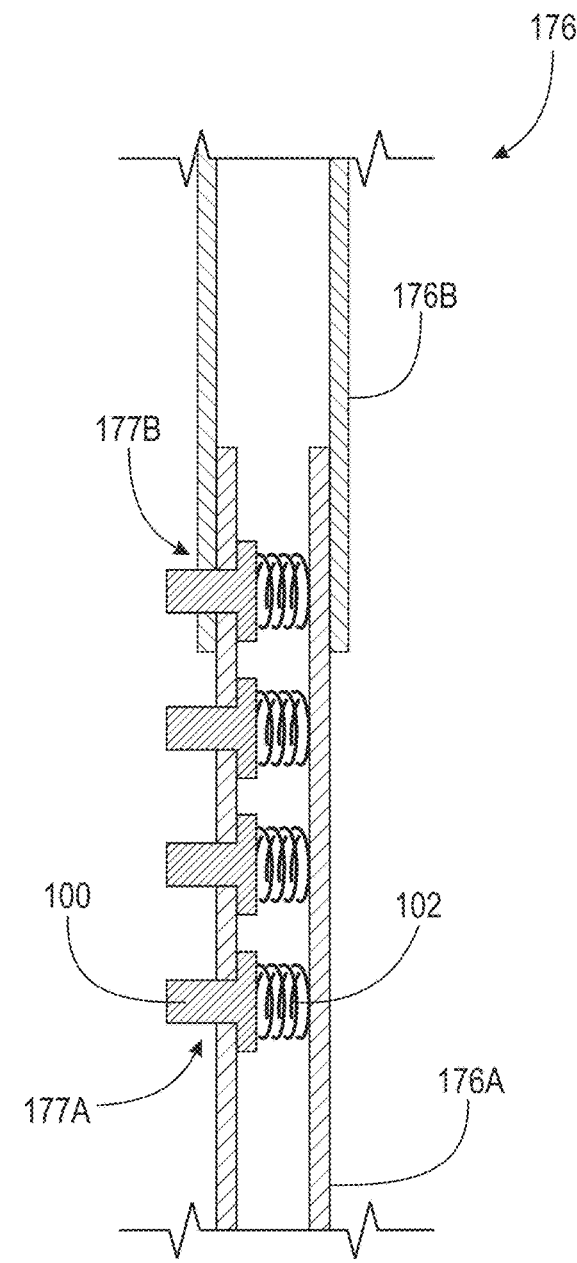
FIG. 13B is a cross-sectional view of a vertical member taken generally along line 13B-13B in FIG. 8.

FIG. 13B is a cross-sectional view of vertical member 176 taken generally along line 13B-13B in FIG. 8. As shown, vertical member 176 comprises inner bar 176A arranged to slidingly engage outer bar 176B (i.e., vertical member 176 is a telescoping bar). In the embodiment shown, inner bar 176A comprises a plurality of pins 100 and corresponding spring members 102. Pins 100 protrude from holes 177A in inner bar 176A, specifically, pins 100 are forced radially outward through holes 177A by spring members 102. Pins 100 are forced radially inward such that inner bar 176A can be slid axially within outer bar 176B. One of pins 100 is aligned with hole 177B in outer bar 176B once the desired length of vertical member 176 is achieved. In an example embodiment, vertical member is cylindrical, inner bar 176A comprises radially outer threading, and outer bar 176B comprises radially inner threading such that the length of vertical member 176 is adjustable by rotating one of inner bar 176A or outer bar 176B relative to the other. It should be appreciated that telescoping members are known in the art and that any suitable telescoping design may be used.

Figure 14:
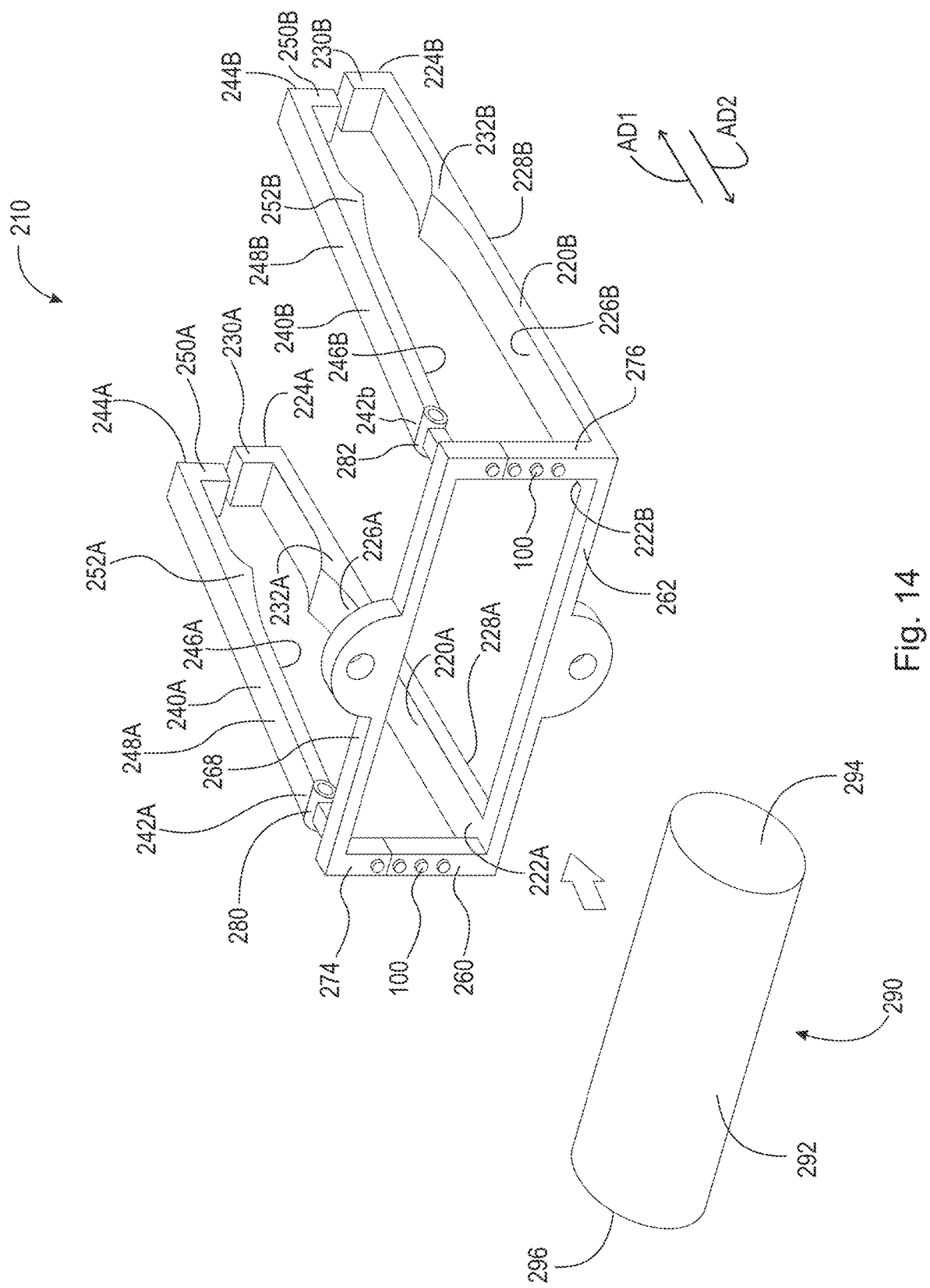
FIG. 14 is a top perspective view of an expandable intervertebral implant in a collapsed state.

FIG. 14 is a top perspective view of expandable intervertebral implant 210 in a collapsed state. Expandable intervertebral implant 210 generally comprises inferior components 220A and 220B, superior components 240A and 240B, support component 260, and wedging component 290.

Inferior component 220A comprises end 222A, end 224A, top surface 226A, and bottom surface 228A. Inferior component 220A is connected to support component 260 at end 222A. In an example embodiment, inferior component 220A is secured to cross member 262 such that it is perpendicular to vertical members 274 and 276. In an example embodiment, inferior component 220A is secured to support component 260 at a non-perpendicular angle to vertical members 274 and 276. Top surface 226A further comprises lip 230A and stop 232A. Lip 230A extends upward from top surface 226A and is arranged generally proximate end 224A. Lip 230A is arranged as a boundary for wedging component 290 (i.e., to keep wedging component 290 within expandable intervertebral implant 210). Stop 232A extends upward from top surface 226A and is arranged axially inward (i.e., in axial direction AD2) from end 224A as shown in FIG. 14. Stop 232A is designed to allow wedging component 290 to move in axial direction AD1, but once beyond stop 232A, to prevent movement of wedging component 290 in axial direction AD2 and maintain its position.

Inferior component 220B comprises end 222B end 224B, top surface 226B, and bottom surface 228B. Inferior component 220B is connected to support component 260 at end 222B. In an example embodiment, inferior component 220B is secured to cross member 262 such that it is perpendicular to vertical members 274 and 276. In an example embodiment, inferior component 220B is secured to support component 260 at a non-perpendicular angle to vertical members 274 and 276. Top surface 226B further comprises lip 230B and stop 232B. Lip 230B extends upward from top surface 226B and is arranged generally proximate end 224B. Lip 230B is arranged as a boundary for wedging component 290 (i.e., to keep wedging component 290 within expandable intervertebral implant 210). Stop 232B extends upward from top surface 226B and is arranged axially inward (i.e., in axial direction AD2) from end 224B as shown in FIG. 14. Stop 232B is designed to allow wedging component 290 to move in axial direction AD1, but once beyond stop 232B, to prevent movement of wedging component 290 in axial direction AD2 and maintain its position.

Superior component 240A comprises end 242A, end 244A, top surface 248A, and bottom surface 246A. Superior component 240A is connected to support component 260 generally at end 242A. Specifically, superior component 240A is connected to hinge 280, and hinge 280 is connected to support component 260. In an example embodiment, hinge 280 is connected to cross-member 268. In an example embodiment, expandable intervertebral implant 210 comprises one or more hinges. Bottom surface 246A further comprises lip 250A and stop 252A. Lip 250A extends downward from bottom surface 246A and is arranged generally proximate end 244A. Lip 250A is arranged as a boundary for wedging component 290 (i.e., to keep wedging component 290 within expandable intervertebral implant 210). Stop 252A extends downward from bottom surface 246A and is arranged axially inward (i.e., in axial direction AD2) from end 244A as shown in FIG. 14. Stop 252A is designed to allow wedging component 290 to move in axial direction AD1, but once beyond stop 252A, to prevent movement of wedging component 290 in axial direction AD2 and maintain its position.

Superior component 240B comprises end 242B, end 244B, top surface 248B, and bottom surface 246B. Superior component 240B is connected to support component 260 generally at end 242B. Specifically, superior component 240B is connected to hinge 282, and hinge 282 is connected to support component 260. In an example embodiment, hinge 282 is connected to cross-member 268. In an example embodiment, expandable intervertebral implant 210 comprises one or more hinges. Bottom surface 246B further comprises lip 250B and stop 252B. Lip 250B extends downward from bottom surface 246B and is arranged generally proximate end 244B. Lip 250B is arranged as a boundary for wedging component 290 (i.e., to keep wedging component 290 within expandable intervertebral implant 210). Stop 252B extends downward from bottom surface 246B and is arranged axially inward from end 244B (i.e., in axial direction AD2) as shown in FIG. 14. Stop 252B is designed to allow wedging component 290 to move in axial direction AD1, but once beyond stop 252B, to prevent movement of wedging component 290 in axial direction AD2 and maintain its position.

It should be appreciated that the orientation of hinges 280 and 282 can be reversed such that inferior components 220A and 220B are hingedly connected to support component 260. In this embodiment, superior components 240A and 240B are connected to support component 260. Specifically, ends 242A and 242B are secured to cross-member 268 such that superior components 240A and 240B are generally perpendicular to vertical members 274 and 276. In an example embodiment, superior components 240A and 240B can each be secured to support component 260 at a non-perpendicular angle to vertical members 274 and 276. Hinges 280 and 282 are secured to cross-member 262, and ends 222A and 222B are secured to hinges 280 and 282, respectively. Additionally, it should be appreciated that in an example embodiment, inferior components 220A and 220B and superior components 240A and 240B are hingedly connected to support component 260.

Support component 260 generally comprises cross-member 262, cross-member 268, vertical member 274, and vertical member 276. Cross-member 262 further comprises flange 264 having through-bore 266 for anchoring expandable intervertebral implant 210 to the vertebrae and prevent expulsion of expandable intervertebral implant 210 as wedging component 290 is advanced therein. Flange 264 extends generally downward from cross-member 262. Cross-member 268 further comprises flange 270 having through-bore 272 for anchoring expandable intervertebral implant 210 to the vertebrae and prevent expulsion of expandable intervertebral implant 210 as wedging component 290 is advanced therein. Flange 270 extends generally upward from cross-member 268. Vertical members 274 and 276 connect cross-member 268 to cross-member 262. Vertical members 274 and 276 are generally adjustable (i.e., can be lengthened or shortened) as was previously discussed with respect to vertical members 174 and 176. In an example embodiment, vertical members 274 and 276 are telescoping bars and have locking mechanism for setting them at a determined length.

Wedging component 290 is generally cylindrical comprising radially outward facing surface 292, end surface 294, and end surface 296. Wedging component 290 is designed to be inserted into expandable intervertebral implant 210 in axial direction AD1 with end surfaces 294 and 296 generally perpendicular to, for example, ends 222A and 224A. As wedging component 290 is advanced in expandable intervertebral implant 210, radially outward facing surface 292 slides along top surfaces 226A-B and bottom surfaces 246A-B, thereby forcing superior components 240A-B upward and away from inferior components 220A-B. Once wedging component 290 passes stops 232A-B and 252A-B, wedging component 290 is prevented from movement in axial direction AD2, unless superior components 240A-B are forced further in the upward direction, thereby releasing stops 232A-B and 252A-B (wedging component 290 can then be removed from expandable intervertebral implant 210). Lips 230A-B and 250A-B also provide an axial boundary preventing wedging component 290 from "falling out" of expandable intervertebral implant 210 in axial direction AD1. Inferior components 220A-B and superior components 240A-B may further comprise lateral rails for end surfaces 294 and 196 to slide against to help ensure that wedging component 290 does not yaw (i.e., twist or oscillate about a vertical axis) as it is being advanced within expandable intervertebral implant 210 (i.e., keep end surfaces 294 and 296 perpendicular to ends 222A and 224B). It should be appreciated that wedging component 290 can be any shape suitable to slide along top surfaces 226A-B and bottom surfaces 246A-B and expand expandable intervertebral implant 210, such as rectangular prism, elliptical prism, triangular prism, spherical, etc. It should also be appreciated that the size of wedging component 290 should be relative to the vertical height of support component 260. When wedging component 290 is fully inserted in expandable intervertebral implant 210, it is desired that superior components 240A-B are substantially parallel to inferior components 120A-B. Therefore, the diameter of wedging component 290 should be slightly less than the vertical length of vertical members 274 and 276. Since vertical members 274 and 276 are adjustable, as previously discussed with respect to vertical members 174 and 176, a variety of sizes of wedging component 290 should be available such that the surgeon can choose the correct size during operation. Additionally, in an example embodiment, support component 260 is laterally expandable. Specifically, cross-members 262 and 268 are adjustable similar to that of vertical members 174 and 176 as previously discussed.

Figure 15A:
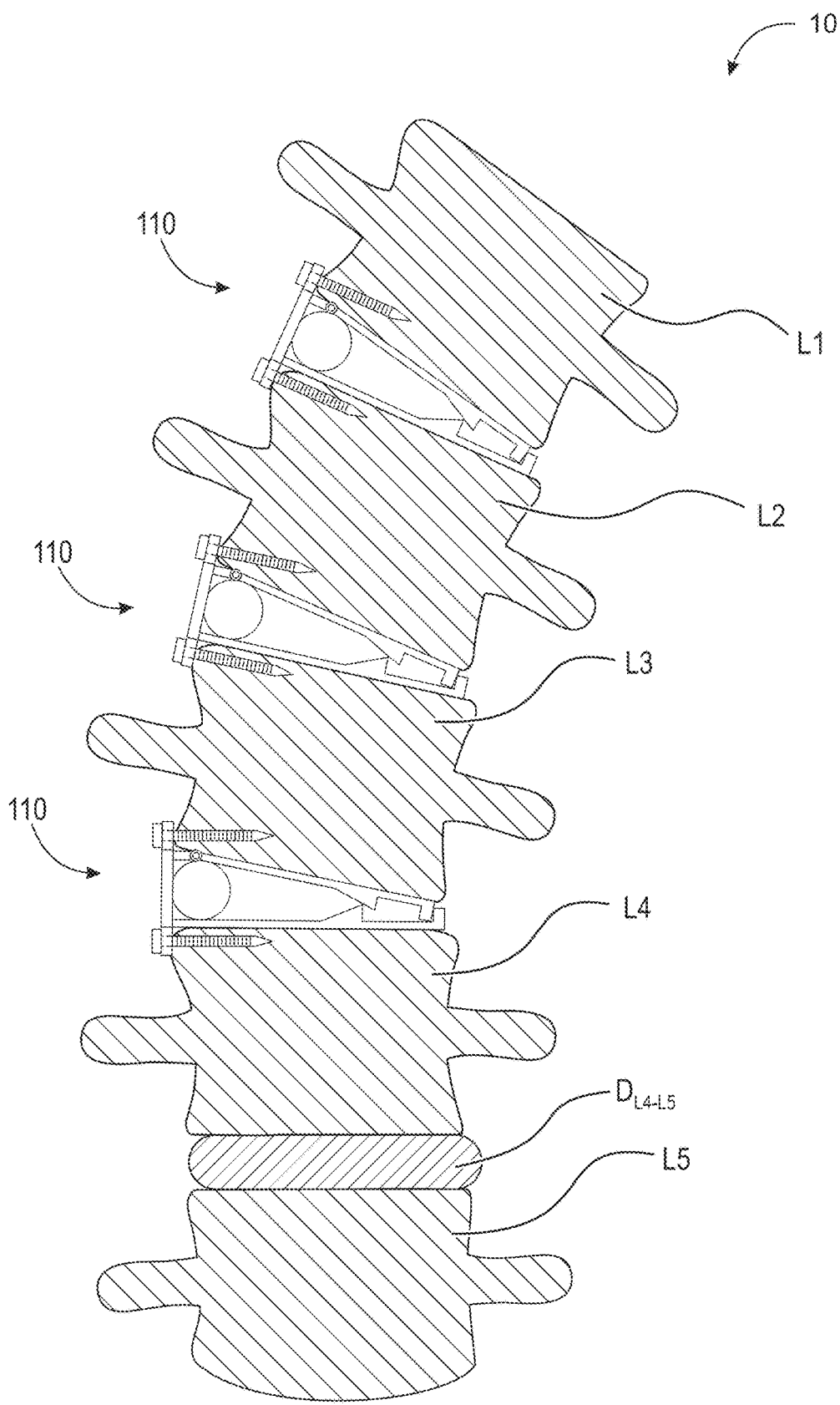
FIG. 15A is a side elevational view of a plurality of expandable intervertebral implants secured in a spinal column in a collapsed state.
Figure 15B:
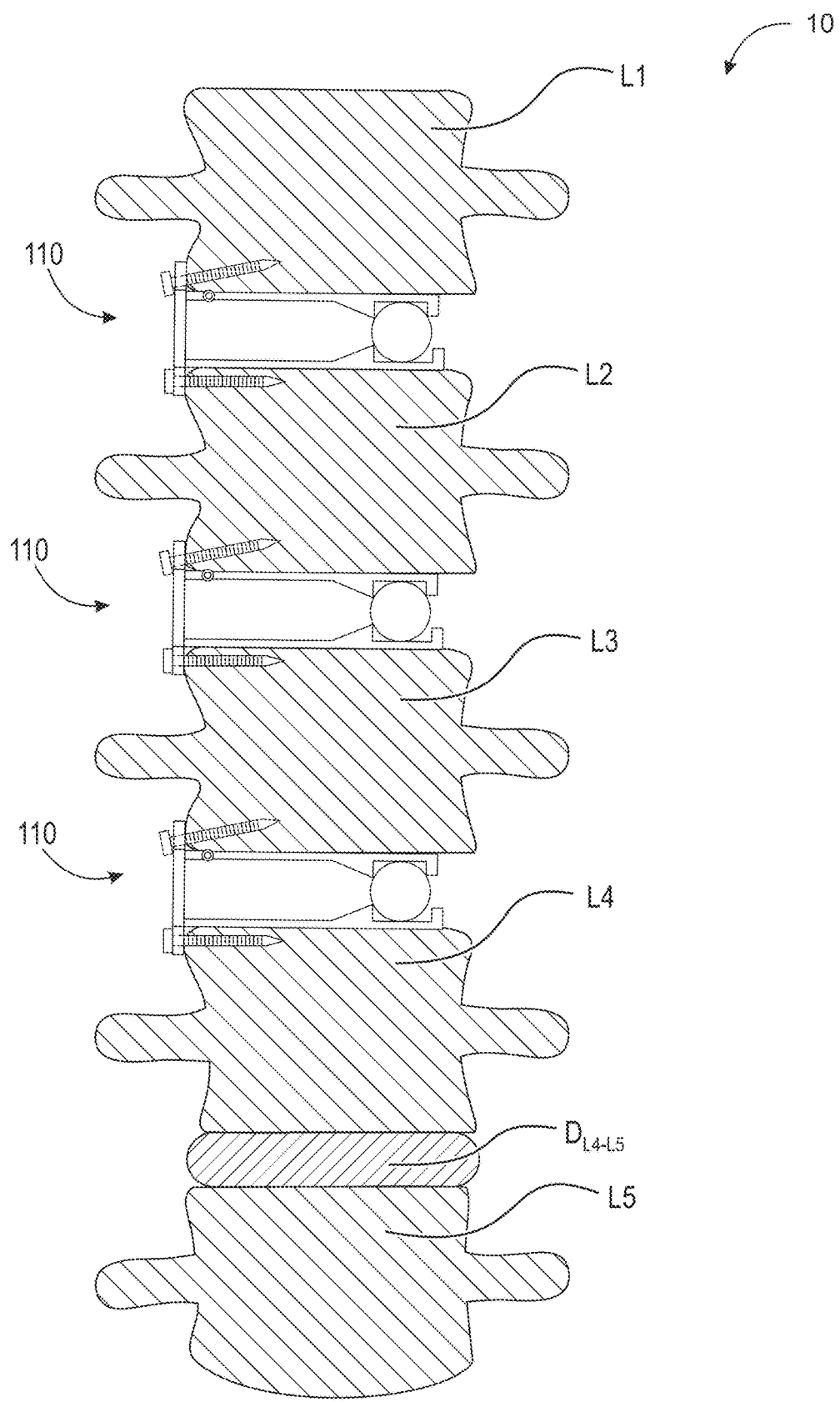
FIG. 15B is a side elevational view of the plurality of expandable intervertebral implants secured in a spinal column, as shown in FIG. 15A, in an expanded state.

FIG. 15A is a side elevational view of a plurality of expandable intervertebral implants 110 secured in spinal column 10 in a collapsed state. Expandable intervertebral implants 110 are inserted between lumbar vertebrae L1-L4 and secured thereto. FIG. 15B is a side elevational view of the plurality of expandable intervertebral implants 110, as shown in FIG. 15A, secured in spinal column 10 in an expanded state. As each of expandable intervertebral implants 110 are expanded (i.e., wedging component 90 is advanced therein), lumbar vertebrae L1-L4 align and spinal column 10 straightens.

Figure 16A:
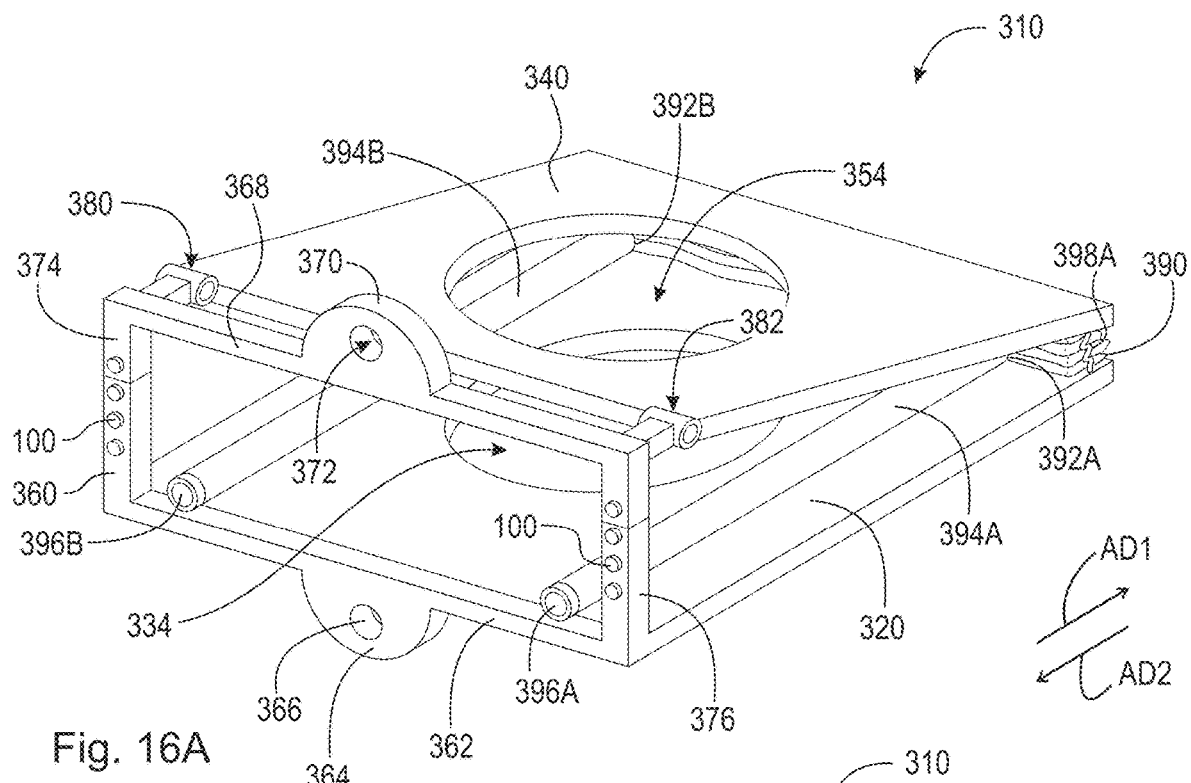
FIG. 16A is a top perspective view of an expandable intervertebral implant, in a collapsed state.
Figure 16B:
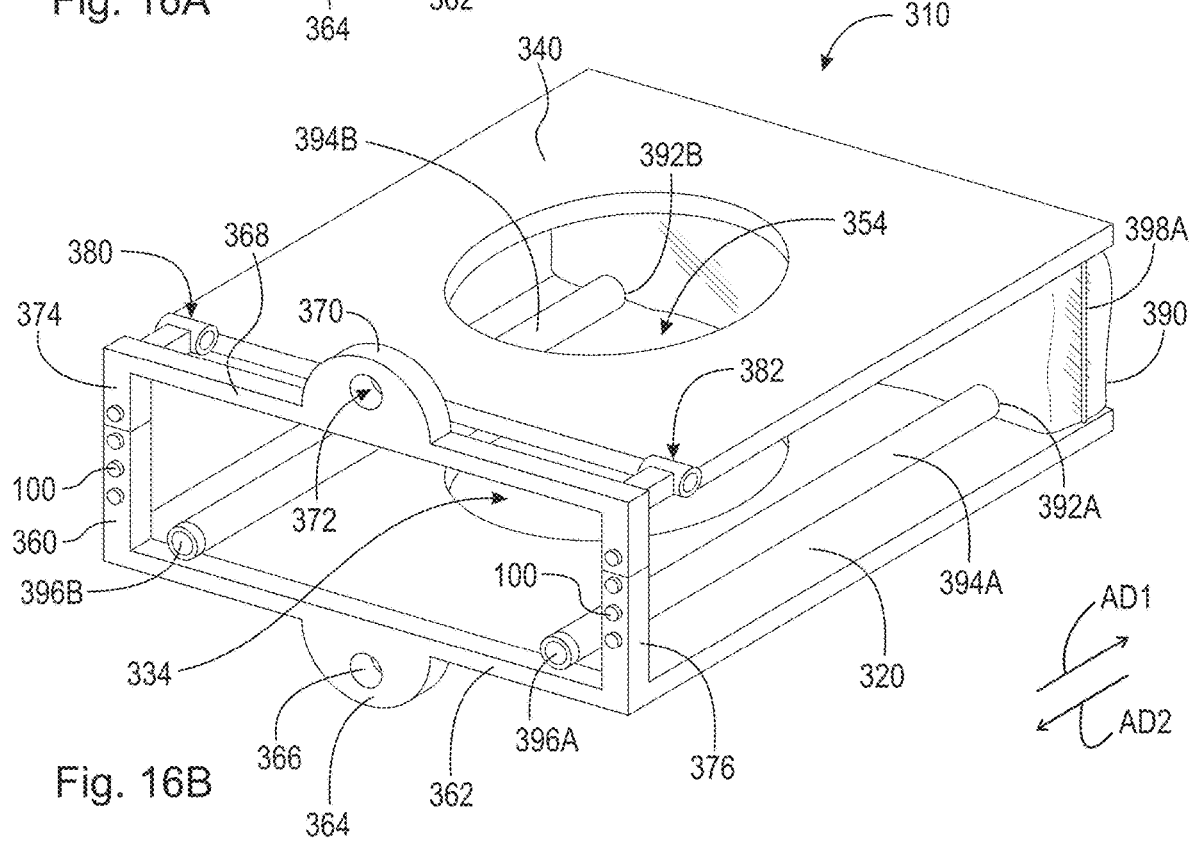
FIG. 16B is a top perspective view of the expandable intervertebral implant shown in FIG. 16A, in an expanded state.
Figure 17A:
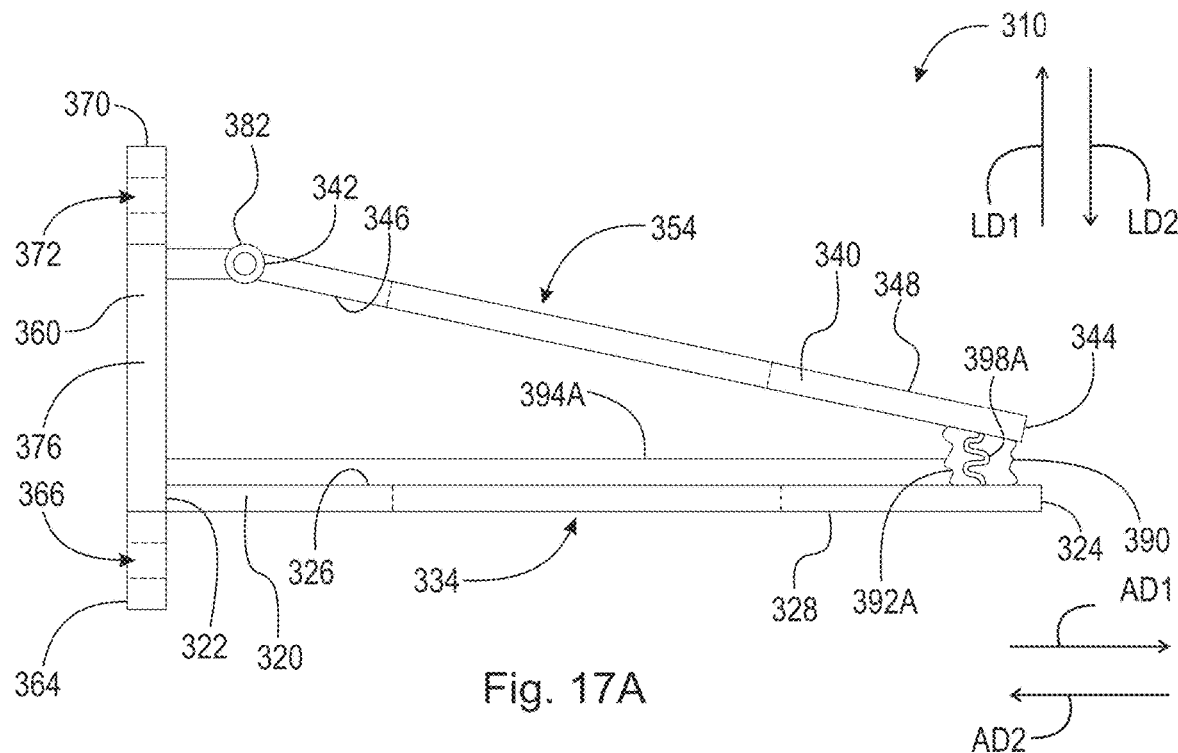
FIG. 17A is a side elevational view of the expandable intervertebral implant shown in FIG. 16A; and, FIG. 17B is a side elevational view of the expandable intervertebral implant shown in FIG. 16B.
Figure 17B:
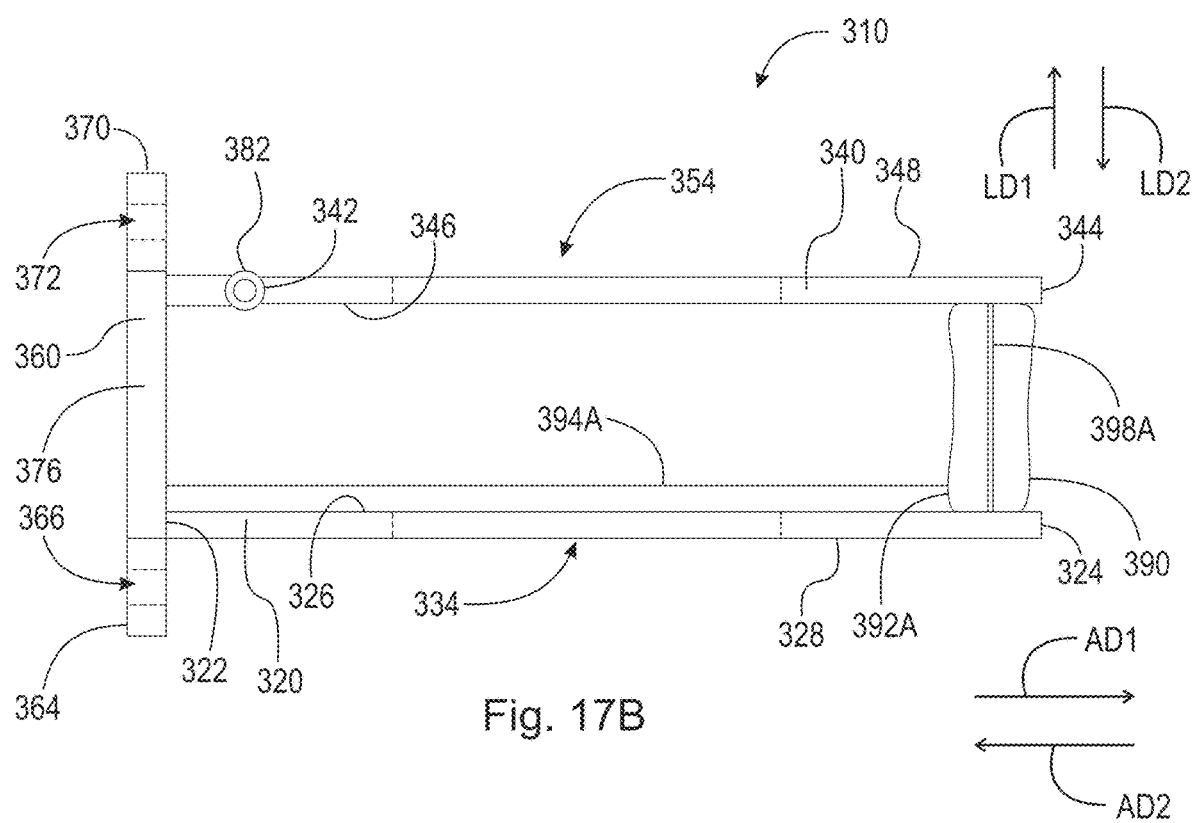

FIG. 16A is a top perspective view of expandable intervertebral implant 310, in a collapsed state. FIG. 16B is a top perspective view of the expandable intervertebral implant 310, in an unexpanded state. FIG. 17A is a side elevational view of expandable intervertebral implant 310, in the collapsed state. FIG. 17B is a side elevational view of expandable intervertebral implant 310, in the expanded state.

Expandable intervertebral implant 310 generally comprises inferior component 320, superior component 340, support component 360, and an expansion mechanism, or balloon 390. It should be appreciated that any expansion mechanism can be used in addition to or in place of the balloon. For example, expansion mechanism 390 may include a scissor jack, a bottle jack, a screw jack, a worm screw jack, etc. Additionally, expansion mechanism 390 may comprise a resilient material that can be compressed and held in a compressed state, and once released from its compressed state, the resilient material expands and thus expands expandable intervertebral implant 310. In some embodiments, expansion mechanism 390 comprises Nickel titanium or Nitinol (part of shape memory alloy), which is a metal alloy of nickel and titanium. In such embodiments, the Nitinol or other shape memory material undergoes deformation (e.g., at a first temperature) and then recovers its original, undeformed shape (e.g., at a second temperature). In other embodiments, the shape memory material is able to recover its original, undeformed shape without the need for temperature change.

Inferior component 320 comprises end 322, end 324, top surface 326, and bottom surface 328. Inferior component 320 is connected to support component 360 at end 322. In an example embodiment, inferior component 320 is secured to cross member 362 such that it is perpendicular to vertical members 374 and 376. In an example embodiment, inferior component 320 is secured to support component 360 at a non-perpendicular angle to vertical members 374 and 376. Inferior component 320 may further comprise aperture 334, which extends from top surface 326 to bottom surface 328. Aperture 334 allows bony or biologic materials placed within expandable intervertebral implant 310, once expanded, to have close apposition to adjacent vertebral endplates and thereby foster interbody fusion.

Superior component 340 comprises end 342, end 344, top surface 348, and bottom surface 346. Superior component 340 is connected to support component 360 generally at end 342. Specifically, superior component 340 is connected to hinges 380 and 382, and hinges 380 and 382 are connected to support component 360. In an example embodiment, hinges 380 and 382 are connected to cross-member 368. In an example embodiment, expandable intervertebral implant 310 comprises one or more hinges. Superior component 340 may further comprise aperture 354, which extends from top surface 348 to bottom surface 346. Aperture 354 allows bony or biologic materials placed within expandable intervertebral implant 310, once expanded, to have close apposition to adjacent vertebral endplates and thereby foster interbody fusion.

It should be appreciated that the orientation of hinges 380 and 382 can be reversed such that inferior component 320 is hingedly connected to support component 360. In this embodiment, superior component 340 is connected to support component 360. Specifically, end 342 is secured to cross-member 368 such that superior component 340 is generally perpendicular to vertical members 374 and 376. In some embodiments, superior component 340 can be secured to support component 360 at a non-perpendicular angle (i.e., non-perpendicular to vertical members 374 and 376). Hinges 380 and 382 are secured to cross-member 362 and end 322 of inferior component 320 is secured to hinges 380 and 382. In an example embodiment, both inferior component 320 and superior component 340 are hingedly connected to support component 360.

Support component 360 generally comprises cross-member 362, cross-member 368, vertical member 374, and vertical member 376. It should be appreciated that support component 360 is substantially similar to support component 160 shown in FIGS. 8 and 9A-B. Cross-member 362 further comprises flange 364 having through-bore 366 for anchoring expandable intervertebral implant 310 to a vertebra and prevent expulsion of expandable intervertebral implant 310 as balloon 390 is expanded or inflated therein. Flange 364 extends generally downward from cross-member 362. Cross-member 368 further comprises flange 370 having through-bore 372 for anchoring expandable intervertebral implant 310 to a vertebra and prevent expulsion of expandable intervertebral implant 310 as balloon 190 is expanded or inflated therein. Flange 368 extends generally upward from cross-member 368. Vertical members 374 and 376 connect cross-member 368 to cross-member 362. Vertical members 374 and 376 are generally adjustable (i.e., can be lengthened or shortened) as was previously discussed with respect to FIGS. 13A and 13B.

Balloon 390 is generally an elastomeric balloon comprising one or more ports, for example, ports 392A and 392B. Balloon 390 is designed to be expanded or inflated in expandable intervertebral implant 310 generally in longitudinal direction LD1 or longitudinal direction LD1. Balloon 390 is connected to top surface 326 of inferior component 320 and bottom surface 346 of superior component 340 proximate to or at ends 324 and 344. In some embodiments, balloon 390 is connected to inferior component at a position between ends 322 and 324 and connected to superior component at a position between ends 342 and 344. As balloon 390 is inflated or expanded in expandable intervertebral implant 310, superior component 340 is forced upward (e.g., in longitudinal direction LD1) and away from superior component 320. Balloon 390 comprises ports 392A and 392B through which fluid is introduced to inflate or expand balloon 390. Expandable intervertebral implant 390 may further comprise one or more tubes, for example, tubes 394A and 394B, connected to the one or more ports. Tubes 394A and 394B are connected to ports 392A and 392B, respectively. Tubes 394A and 394B comprise openings 396A and 396B. Fluid can be injected in direction AD1 through openings 396A-B, tubes 394A-B, and ports 392A-B. The fluid may be, for example, hardenable such that once expandable intervertebral implant 310 is expanded to a suitable height, the fluid can be allowed to harden and permanently set such height. It should be appreciated that although tubes 394A-B are shown positioned along top surface 326, they can be provided at any suitable position. For example, in some embodiments, tubes 394A-B are positioned at least partially within inferior component 320 between top surface 326 and bottom surface 328. In some embodiments, tubes 394A-B are positioned at least partially within superior component 320 between top surface 326 and bottom surface 328. In some embodiments, tubes 394A-B are positioned along bottom surface 346. It should be appreciated that balloon 390 can be any shape suitable to connect to or abut against top surface 326 and bottom surface 346 and expand expandable intervertebral implant 310, such as cylindrical, rectangular prism, elliptical prism, triangular prism, spherical, etc. When balloon 390 is fully inflated or expanded in expandable intervertebral implant 310, it is desired that superior component 340 is substantially parallel to inferior component 320. In some embodiments, balloon 390 further comprises one or more limit cords or filaments, for example, limit cords or filaments 398A and 398B. Limit cords 398A-B are operatively arranged to limit the amount that balloon 390 can be expanded or inflated and/or the distance that superior component 340 can be displaced relative to inferior component. Limit cords 398A-B are generally inelastic. Limit cords 398A-B may be arranged within balloon 390, along the external surface of balloon 390, or separate from balloon 390 between top surface 326 and bottom surface 346. In some embodiments, balloon 390 is fixedly secured to superior component 340 and inferior component 320. In some embodiments, balloon 390 is removably secured to superior component 340 and inferior component 320 such that, for example, balloon 390 can be removed to collapse superior component 340 relative to inferior component 320.

Expandable intervertebral implant 310 can be implanted in a spinal column similarly to expandable intervertebral implant 110 as shown in FIGS. 10 and 11A-B. Expandable intervertebral implant 310 is inserted into the spinal column between, for example, the L3 and L4 vertebrae, or where disc $D_{L3-L4}$ should be. Expandable intervertebral implant 310 is secured to the vertebrae using fasteners (e.g., screws, anchors, bolts, etc., or any other suitable fastening mechanism, including adhesives). Expandable intervertebral implant 310 is then vertically expanded until the desired height is reached. Support component 360 is expanded by lengthening vertical members 374 and 376 to a suitable length, and then fluid is injected into port 392A and/or port 392B to inflate balloon 390 in expandable intervertebral implant 310 until it is fully expanded. Expandable intervertebral implant 310 is then filled with fusion material and left in situ. It should be appreciated that vertical members 374 and 376 can be adjusted to a suitable length prior to inserting expandable intervertebral implant 310 into the spinal column.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

10 Spinal column
12 Ligament
C1-C7 Cervical vertebrae
T1-T12 Thoracic vertebrae
L1-L5 Lumbar vertebrae
S Sacrum
C Coccyx
$D_{L1-L2}$ Disc
$D_{L2-L3}$ Disc
$D_{L3-L4}$ Disc
$D_{L4-L5}$ Disc
F Facet
FJ Facet joint
SP Spinous process
TP Transverse process
IF Intervertebral foramen
NC Neural canal
A Annulus
N Nucleus
DH Disc space height
30 Endoscope
31 Light guide connector
32 Light guide tube
33 Control body
34 Insertion tube
40 Surgeon
42 Monitor
45 Patient
100 Pins
102 Spring members
104 Fastener
106 Fastener
110 Expandable intervertebral (fusion) implant
120 Inferior component
122 End
124 End
126 Top surface
128 Bottom surface
130 Lip
131 Hook
132 Stop
134 Aperture
140 Superior component
142 End
144 End
146 Bottom surface
148 Top surface
150 Lip
151 Hook
152 Stop
154 Aperture
160 Support component
162 Cross-member
164 Flange
166 Through-bore
168 Cross-member
170 Flange
172 Through-bore
174 Vertical member
174A Inner bar
174B Outer bar
175A Holes
175B Hole
176 Vertical member
176A Inner bar
176B Outer bar
177A Holes
177B Hole
180 Hinge
182 Hinge
190 Wedging component
192 Radially outward facing surface
194 End surface
196 End surface
210 Expandable intervertebral (fusion) implant
220A Inferior component
220B Inferior component
222A End
222B End
224A End
224B End
226A Top surface
226A Top surface
228A Bottom surface
228A Bottom surface
230A Lip
230B Lip
232A Stop
232B Stop
240A Superior component
240B Superior component
242A End
242B End
244A End
244B End
246A Bottom surface
246A Bottom surface
248A Top surface
248A Top surface
250A Lip
250B Lip
252A Stop
252B Stop
260 Support component
262 Cross-member
264 Flange
266 Through-bore
268 Cross-member
270 Flange
272 Through-bore
274 Vertical member
276 Vertical member
280 Hinge
282 Hinge
290 Wedging component
292 Radially outward facing surface
294 End surface
296 End surface
310 Expandable intervertebral (fusion) implant
320 Inferior component
322 End
324 End
326 Top surface
328 Bottom surface
334 Aperture
340 Superior component
342 End
344 End 346 Bottom surface
348 Top surface
354 Aperture
360 Support component
362 Cross-member
364 Flange
366 Through-bore
368 Cross-member
370 Flange
372 Through-bore
374 Vertical member
376 Vertical member
380 Hinge
382 Hinge
390 Expansion mechanism or balloon
392A Port
392B Port
394A Tube
394B Tube
396A Opening
396B Opening
398A Limit cord or filament
398B Limit cord or filament (not shown)
AD1 Axial direction
AD2 Axial direction
LD1 Longitudinal direction
LD2 Longitudinal direction

What is claimed is:

1. An expandable intervertebral implant, comprising:
a support component;
an inferior component, including:
  a first proximate end connected to the support component;
  a first distal end;
  a first top surface; and,
  a first bottom surface;
a superior component, including:
  a second proximate end connected to the support component;
  a second distal end;
  a second top surface; and,
  a second bottom surface; and,
a balloon fixedly secured to the first top surface and the second bottom surface and operatively arranged to expand the expandable intervertebral implant.

2. The expandable intervertebral implant as recited in claim 1, wherein the superior component is hingedly connected to the support component.

3. The expandable intervertebral implant as recited in claim 2, wherein the superior component is connected to the support component via one or more hinges.

4. The expandable intervertebral implant as recited in claim 2, wherein the support component comprises:
a first cross-member;
a second cross-member; and,
one or more vertical members connecting the first and second cross-members.

5. The expandable intervertebral implant as recited in claim 4, wherein the first cross-member comprises a first flange having a first through-bore.

6. The expandable intervertebral implant as recited in claim 5, wherein the second cross-member comprises a second flange having a second through-bore.

7. The expandable intervertebral implant as recited in claim 4, wherein each of the one or more vertical members is adjustable in length.

8. The expandable intervertebral implant as recited in claim 7, wherein at least one of the one or more vertical members comprises a plurality of locking pins operatively arranged to lock the one or more vertical members at a length.

9. The expandable intervertebral implant as recited in claim 2, wherein the inferior component further comprises a first aperture and the superior component further comprises a second aperture.

10. The expandable intervertebral implant as recited in claim 2, wherein the balloon comprises at least one port, wherein the at least one port is operatively arranged to allow fluid to be injected into and inflate the balloon.

11. The expandable intervertebral implant as recited in claim 10, further comprising at least one tube connected to the at least one port.

12. The expandable intervertebral implant as recited in claim 2, wherein when the expandable intervertebral implant is in a fully expanded state, the superior component is substantially parallel to the inferior component.

13. The expandable intervertebral implant as recited in claim 1, further comprising at least one limit cord operatively arranged to limit the expansion of the intervertebral implant.

14. An expandable intervertebral fusion implant, comprising:
a support component;
at least one inferior component, including:
  a first proximate end connected to the support component;
  a first distal end;
  a first top surface;
  a first bottom surface; and,
  a first aperture;
at least one superior component, including:
  a second proximate end connected to the support component;
  a second distal end;
  a second top surface;
  a second bottom surface; and,
  a second aperture; and,
an expansion mechanism fixedly secured to the first top surface and the second bottom surface and operatively arranged to be expanded to displace the at least one superior component relative to the at least one inferior component.

15. The expandable intervertebral fusion implant as recited in claim 14, wherein the at least one superior component is hingedly connected to the support component.

16. The expandable intervertebral fusion implant as recited in claim 14, wherein the at least one superior component is connected to the support component via one or more hinges.

17. The expandable intervertebral implant as recited in claim 14, wherein the support component is adjustable in length.

18. The expandable intervertebral implant as recited in claim 14, wherein the expansion mechanism is a balloon comprising at least one port, wherein the at least one port is operatively arranged to allow fluid to be injected into and inflate the balloon.

19. The expandable intervertebral implant as recited in claim 14, further comprising at least one limit cord operatively arranged to limit the displacement of the at least one superior component relative to the at least one inferior component.

20. An expandable intervertebral implant, comprising:
a support component;
an inferior component, including:
- a first proximate end connected to the support component;
- a first distal end;
- a first top surface; and,
- a first bottom surface;

a superior component, including:
- a second proximate end connected to the support component;
- a second distal end;
- a second top surface; and,
- a second bottom surface;

a balloon connected to the first top surface and the second bottom surface and operatively arranged to expand the expandable intervertebral implant; and,
a limit cord operatively arranged to limit the expansion of the intervertebral implant.

* * * * *